(12) United States Patent
Jauriqui

(10) Patent No.: US 9,335,300 B2
(45) Date of Patent: May 10, 2016

(54) SAW MODE-BASED SURFACE DEFECT SYSTEM/METHOD

(71) Applicant: Vibrant Corporation, Albuquerque, NM (US)

(72) Inventor: Leanne Jauriqui, Albuquerque, NM (US)

(73) Assignee: VIBRANT CORPORATION, Albuquerque, NM (US)

( * ) Notice: Subject to any disclaimer, the term of this patent is extended or adjusted under 35 U.S.C. 154(b) by 25 days.

(21) Appl. No.: 14/210,783

(22) Filed: Mar. 14, 2014

(65) Prior Publication Data

US 2014/0305214 A1    Oct. 16, 2014

Related U.S. Application Data

(60) Provisional application No. 61/792,424, filed on Mar. 15, 2013.

(51) Int. Cl.
| | |
|---|---|
| *G01N 29/12* | (2006.01) |
| *G01N 29/04* | (2006.01) |
| *G01N 29/24* | (2006.01) |
| *G01N 29/44* | (2006.01) |

(52) U.S. Cl.
CPC .............. *G01N 29/12* (2013.01); *G01N 29/041* (2013.01); *G01N 29/2462* (2013.01); *G01N 29/4427* (2013.01); *G01N 2291/103* (2013.01); *G01N 2291/265* (2013.01); *G01N 2291/2696* (2013.01)

(58) Field of Classification Search
CPC ..... G01N 29/12; G01N 29/348; G01N 29/42; G01N 29/46; G01N 2291/014; G01N 2291/0423
USPC ............................ 73/579, 587, 623, 648, 659
See application file for complete search history.

(56) References Cited

U.S. PATENT DOCUMENTS

| | | | | |
|---|---|---|---|---|
| 5,062,296 | A | * | 11/1991 | Migliori ........................... 73/579 |
| 5,257,544 | A | * | 11/1993 | Khuri-Yakub et al. ......... 73/579 |
| 5,351,543 | A | | 10/1994 | Migliori et al. |
| 5,355,731 | A | * | 10/1994 | Dixon et al. .................... 73/579 |
| 5,425,272 | A | * | 6/1995 | Rhodes et al. .................. 73/579 |
| 5,631,423 | A | * | 5/1997 | Rhodes ........................... 73/579 |
| 5,837,896 | A | | 11/1998 | Rhodes et al. |
| 7,649,632 | B2 | | 1/2010 | Murray |

(Continued)

OTHER PUBLICATIONS

Hunter, L.J. et al., "Advances in Resonance Based NDT for Ceramic Components", AIP Conference Proceedings, vol. 1430, Jul. 17, 2011-Jul. 22, 2011, pp. 1137-1144 Jul. 17, 2011.
Hsieh C.P., "One-Point Contact Measurement of Spherical Resonances", Applied Physics Letters, AIP, American Institute of Physics, Melville, NY, US, vol. 62, No. 24, Jun. 14, 1993, pp. 3091-3093 Jun. 14, 1993.

(Continued)

*Primary Examiner* — Laura Martin
*Assistant Examiner* — Rose M Miller
(74) *Attorney, Agent, or Firm* — Marsh Fischmann & Breyfogle LLP

(57) ABSTRACT

Various approaches for assessing a part for a defect are disclosed and that are based upon SAW modes. In one embodiment, a part-under-test (120) is excited. One or more SAW modes (206) are identified in the frequency response (240/260) of the part-under-test (120). A SAW mode area (248/266) in the frequency response of the part-under-test (120) is compared with a baseline SAW mode area (238/258) of a baseline frequency response (230/250) (and which may be associated with an acceptable part). This comparison may be used to determine if the part-under-test (120) may be characterized defective in at least some respect.

31 Claims, 17 Drawing Sheets

(56) References Cited

U.S. PATENT DOCUMENTS

| | | |
|---|---|---|
| 8,368,289 B2 | 2/2013 | Karabutov et al. |
| 2006/0027021 A1* | 2/2006 | Choi et al. ............... 73/579 |
| 2011/0238336 A1 | 9/2011 | Di Scalea et al. |
| 2012/0330569 A1 | 12/2012 | Singh et al. |

OTHER PUBLICATIONS

Hsieh C.P. et al., "Surface Defect Inspection of Spherical Objects by the Resonant Sphere Technique", Applied Physics Letters, AIP, American Institute of Physics, Melville, NY, US, vol. 60, No. 15, Apr. 13, 1992, pp. 1815-1817 Apr. 13, 1992.

* cited by examiner

SAW MODE-BASED SURFACE DEFECT SYSTEM/METHOD

CROSS-REFERENCE TO RELATED APPLICATIONS

This patent application is a non-provisional application of, and claims priority to, pending U.S. Provisional Patent Application Ser. No. 61/792,424 that is entitled "SAW MODE-BASED SURFACE DEFECT SYSTEM/METHOD," that was filed on Mar. 15, 2013, and the entire disclosure of which is hereby incorporated by reference in its entirety herein.

STATEMENTS REGARDING FEDERALLY SPONSORED RESEARCH OR DEVELOPMENT

The U.S. Government has a nonexclusive, nontransferable, irrevocable, paid-up license to practice, or have practiced for or on its behalf, the subject invention throughout the world as provided for by the terms of Contract Number N68335-09-C-0159 awarded by Naval Air Warfare Center AD (LKE).

FIELD OF THE INVENTION

The present invention generally relates to the testing of parts for surface defects and, more particularly, to using one or more SAW modes in the assessment of a part for surface defects.

BACKGROUND OF THE INVENTION

A variety of techniques have been developed in which parts may be tested "nondestructively," meaning that the testing methodology enables defects to be identified without causing damage to the part. Examples of such nondestructive-testing methodologies include acoustic techniques, magnetic-particle techniques, liquid-penetrant techniques, radiographic techniques, eddy-current testing, and low-coherence interferometry, among others. There are various known advantages and disadvantages to each of these categories of testing methodologies, which are accordingly used in different environments.

Nondestructive-testing methods that use acoustic radiation generally operate in the ultrasonic range of the acoustic spectrum, and are valuable for a number of reasons. Such techniques are sensitive, for example, to both surface and subsurface discontinuities, enabling identification of defects both within the bulk and near the surface of a part. The depth of penetration for defect detection is generally superior to many other nondestructive-testing methodologies, and the techniques are highly accurate not only in determining the position of a defect, but also in estimating its size and shape.

SUMMARY

A first aspect of the present invention is embodied by an evaluation of a part for the existence of one or more surface defects. A part-under-test is excited using at least one input frequency. A first surface acoustical wave (SAW) mode is identified in a frequency response of the part-under-test to this excitation (hereafter, a "part-under-test or PUT frequency response"). A first SAW mode area in the PUT frequency response is compared to a baseline SAW mode area in a baseline frequency response (e.g., a frequency response that is equated with an acceptable part). A defect assessment of the part-under-test uses this comparison.

A number of feature refinements and additional features are applicable to the first aspect of the present invention. These feature refinements and additional features may be used individually or in any combination. The following discussion is applicable to the first aspect, up to the start of the discussion of a second aspect of the present invention.

The baseline SAW mode area of the baseline frequency response may be for a SAW mode in the baseline frequency response that corresponds with the first SAW mode in the PUT frequency response. The first SAW mode area in the PUT frequency response may include the area encompassed by the first SAW mode. The SAW mode in the baseline frequency response encompassed by the baseline SAW mode area may include at least some of the same frequencies as the first SAW mode included in the first SAW mode area.

The comparison may entail identifying first and second assessment frequencies within the baseline frequency response, as well as identifying third and fourth assessment frequencies within the PUT frequency response. The magnitude of the second assessment frequency may be larger than the magnitude of the first assessment frequency (each being associated with the baseline frequency response), the magnitude of the fourth assessment frequency may be larger than the magnitude of the third assessment frequency (each being associated with the PUT frequency response), or both. The first and second assessment frequencies may at least generally define boundaries for the baseline SAW mode area in the baseline frequency response. In one embodiment, the first and second assessment frequencies are at least generally adjacent to a "zero slope" region of the baseline frequency response.

The third and fourth assessment frequencies (each being associated with the PUT frequency response) may encompass the first SAW mode area. The fourth assessment frequency may define one of the boundaries (e.g., the higher frequency boundary) for the first SAW mode area. In one embodiment, the fourth assessment frequency is at least generally adjacent to a "zero slope" region of the baseline frequency response. In any case, a relationship of the first and second assessment frequencies for the baseline SAW mode area (associated with the baseline frequency response) may be compared to a relationship of the third and fourth assessment frequencies for the first SAW mode area (associated with the PUT frequency response). In the event that the part-under-test has one or more surface defects, the first SAW mode in the PUT frequency response may be "compressed" (compared to the corresponding SAW mode in the baseline frequency response) and which may result in the development of one or more degenerate peaks at lower frequencies than the first SAW mode. Therefore, the third assessment frequency in the PUT frequency response may move to a lower frequency than the first assessment frequency in the baseline frequency response.

The part-under-test may be characterized as being defective based upon satisfaction of a surface defect condition. At least part of this surface defect trigger condition may be satisfied when the relationship of the third and fourth assessment frequencies for the first SAW mode area (associated with the PUT frequency response) satisfies a first threshold that is based upon the relationship of the first and second assessment frequencies for the baseline frequency response. For instance, the assessment may entail determining a second differential between the fourth and third assessment frequencies for the first SAW mode area (associated with the PUT frequency response; e.g., subtracting the third assessment frequency from the fourth assessment frequency; taking the absolute value of the difference between the third and fourth assessment frequencies), and determining a first differential between the second and first assessment frequencies for the baseline SAW mode area (associated with the baseline frequency response; e.g., subtracting the first assessment frequency from the second assessment frequency; taking the absolute value of the difference between the first and second assessment frequencies). Having the second differential be at least a predetermined amount larger than the first differential may be equated with a surface defect condition. Having the second differential satisfy the first threshold (which again is based upon the first differential) may be equated with a surface defect condition. The first threshold may require the second differential to be at least a predetermined amount larger than the first differential in order to be applicable to satisfaction of the surface defect trigger condition. One or more surface defect conditions may be required to exist in order to satisfy the surface defect trigger condition.

A surface defect condition may be equated as existing when there is a predetermined relationship between the noted second differential (between the fourth and third assessment frequencies for the first SAW mode area associated with the PUT frequency response) and the noted first differential (between the second and first assessment frequencies for the baseline SAW mode area associated with the baseline frequency response). A surface defect condition may be equated with the second differential being at least 15% larger than the first differential in one embodiment, and with the second differential being at least 30% larger than the first differential in another embodiment. A surface defect condition may be equated with the first differential being no more than 70% of the second differential in one embodiment, and with the first differential being no more than 85% of the second differential in another embodiment.

A surface defect trigger condition may be satisfied based solely on the existence of a single surface defect condition (e.g., the second differential need only be at least a predetermined amount larger than the first differential for a single SAW mode). However, the surface defect trigger condition could be configured so as to require that a predetermined number of multiple surface defect conditions exist in order for the surface defect trigger condition to be satisfied (e.g., the second differential may need to be at least a predetermined amount larger than the first differential for each of a predetermined number of different SAW modes).

The first and second assessment frequencies for the baseline SAW mode area (associated with the baseline frequency response) may be within a reference frequency range. The third and fourth assessment frequencies for the first SAW mode may be within this same reference frequency range of the PUT frequency response. In one embodiment, this reference frequency range includes a single SAW mode. In any case, values for the first and second assessment frequencies may be derived such that the baseline SAW mode area is a predetermined percentage of an area of the baseline frequency response over the reference frequency range. This "predetermined percentage" may be any appropriate value. One embodiment has the first and second assessment frequencies being selected such that the baseline SAW mode area is a majority of the area of the baseline frequency response over the reference frequency range. Another embodiment has the first and second assessment frequencies being selected such that the baseline SAW mode area is 95% of the area of the baseline frequency response over the reference frequency range. Yet another embodiment has the first and second assessment frequencies being selected such that the baseline SAW mode area is 99% of the area of the baseline frequency response over the reference frequency range.

Values for the third and fourth assessment frequencies may be derived such that the first SAW mode area is the same predetermined percentage (used above for the selection of the first and second assessment frequencies) of an area of the PUT frequency response over the reference frequency range (e.g., third and fourth assessment frequencies may be selected so that the first SAW mode area is the same size as the baseline SAW mode area). If there are one or more defects in the part-under-test, the SAW mode being analyzed in the PUT frequency response may be at least somewhat "compressed" compared to this same SAW mode in the baseline frequency response, such that the value of the third assessment frequency (in the PUT frequency response) is smaller than the value of the first assessment frequency (in with the baseline frequency response).

Another approach of using the above-noted first, second, third, and fourth assessment frequencies to identify a defect in a part-under-test may entail deriving values for the third and fourth assessment frequencies (associated with the PUT frequency response) such that the first SAW mode area is equal to the baseline SAW mode area. A reference frequency within the baseline frequency response may be selected so as to be between the first and second assessment frequencies (associated with the baseline frequency response). This same reference frequency may be identified in the PUT frequency response, and may be compared with each of the third and fourth assessment frequencies for the purpose of assessing the PUT for one or more defects.

The reference frequency may be selected such that a first area of the baseline frequency response (between the first assessment frequency and the reference frequency) is equal to a second area of the baseline frequency response (between the reference frequency and the second assessment frequency). Other reference frequencies may be appropriate. The first and second assessment frequencies (associated with the baseline frequency response) may be selected so as to include the SAW mode that corresponds to the first SAW mode in the PUT frequency response. In one embodiment, the first and second assessment frequencies are at least generally adjacent to a "zero slope" region of the baseline frequency response. In one embodiment, the first and second assessment frequencies at least generally define the boundaries of a SAW mode that corresponds to the first SAW mode in the PUT frequency response.

The part-under-test may be characterized as being defective based upon satisfaction of a surface defect trigger condition. At least part of the surface defect trigger condition may be satisfied when a first differential (between the reference frequency and the third assessment frequency) satisfies a first threshold that is based upon a second differential (between the fourth assessment frequency and the same reference frequency). For instance, at least part of the surface defect trigger condition may be satisfied when a first differential (between the reference frequency and the third assessment frequency) is at least a predetermined amount larger than a second differential (between the fourth assessment frequency and the same reference frequency). In one embodiment, the above-noted first threshold is at least about 100% (e.g., the difference between the reference frequency and the third assessment frequency may be required to be at least twice as large as the difference between the fourth assessment frequency and the reference frequency in order to be equated with a surface defect condition). In one embodiment, this first threshold is at least about 150% (e.g., the difference between the reference frequency and the third assessment frequency may be required to be at least 2.5 times as large as the difference between the fourth assessment frequency and the reference frequency in order to be equated with a surface defect condition). One or more surface defect conditions may be required to exist in order to satisfy the surface defect trigger condition.

A surface defect condition may be equated as existing when there is a predetermined relationship between the noted second differential (between the fourth assessment frequency and the reference frequency) and the noted first differential (between the same reference frequency and the third assessment frequency). A surface defect condition may be equated with the first differential being at least 100% larger than the second differential in one embodiment, with the first differential being at least 150% larger than the second differential in another embodiment, with the first differential being at least 50% larger than the second differential in another embodiment, and with the first differential being at least 25% larger than the second differential in another embodiment. A surface defect condition may be equated with the second differential being no more than 50% of the first differential in one embodiment, and with the second differential being no more than 40% of the first differential in another embodiment.

A surface defect trigger condition may be satisfied based solely on the existence of a single surface defect condition (i.e., in relation to a single SAW mode); the first differential being at least a predetermined amount larger than the second differential for a single SAW mode in the PUT frequency response). However, the surface defect trigger condition could be configured so as to require that a predetermined number of multiple surface defect conditions exist in order for the surface defect trigger condition to be satisfied (e.g., a surface defect condition in accordance with the foregoing may be required to exist for a predetermined number of different SAW modes; the first differential being at least a predetermined amount larger than the second differential may be required for each of a plurality of different SAW modes in the PUT frequency response).

A second aspect of the present invention is embodied by an evaluation of a part for the existence of one or more surface defects. First and second assessment frequencies within a reference frequency range of a baseline frequency response (e.g., a frequency response that is equated with an acceptable part) are derived. This reference frequency range includes a first surface acoustical wave (SAW) mode. A part-under-test is excited using at least one input frequency. The corresponding first SAW mode is identified in a frequency response of the part-under-test to this excitation (hereafter, a "part-under-test or PUT frequency response"). Third and fourth assessment frequencies within the PUT frequency response are derived. These third and fourth assessment frequencies are within the same reference frequency range and encompass the corresponding first SAW mode. A first differential between the first and second assessment frequencies (associated with the baseline frequency response; e.g., the second assessment frequency, minus the first assessment frequency) is determined (e.g., derived; calculated). A second differential between the third and fourth assessment frequencies (associated with the PUT frequency response; e.g., the fourth assessment frequency, minus the third assessment frequency) is determined (e.g., derived; calculated). A comparison of the second differential to a first threshold is undertaken, where this first threshold is based upon the first differential. The part-under-test is characterized as being defective based upon satisfaction of a surface defect trigger condition. At least part of this surface defect trigger condition may be satisfied when the second differential (associated with the PUT frequency response) satisfies the first threshold (which again is based upon the first differential (associated with the baseline frequency response)).

A number of feature refinements and additional features are applicable to the second aspect of the present invention. These feature refinements and additional features may be used individually or in any combination. The following discussion is applicable to the second aspect, up to the start of the discussion of a third aspect of the present invention.

Values for the first and second assessment frequencies may be derived such that an area between the first and second assessment frequencies is a predetermined percentage of an area of the baseline frequency response over the reference frequency range. This "predetermined percentage" may be of any appropriate value. One embodiment has the first and second assessment frequencies being selected such the area of the baseline frequency response between the first and second assessment frequencies is a majority of the area of the baseline frequency response over the reference frequency range. Another embodiment has the first and second assessment frequencies being selected such that the area of the baseline frequency response between the first and second assessment frequencies is 95% of the area of the baseline frequency response over the reference frequency range. Another embodiment has the first and second assessment frequencies being selected such the area of the baseline frequency response between the first and second assessment frequencies is 99% of the area of the baseline frequency response over the reference frequency range.

The magnitude of the second assessment frequency may be larger than the magnitude of the first assessment frequency (each being associated with the baseline frequency response), the magnitude of the fourth assessment frequency may be larger than the magnitude of the third assessment frequency (each being associated with the PUT frequency response), or both. The first and second assessment frequencies may at least generally define boundaries for the first SAW mode in the baseline frequency response. In one embodiment, the first and second assessment frequencies are at least generally adjacent to a "zero slope" region of the baseline frequency response.

The third and fourth assessment frequencies (each being associated with the PUT frequency response) may encompass the corresponding SAW mode. The fourth assessment frequency may define one of the boundaries (e.g., the higher frequency boundary) for the corresponding SAW mode. In one embodiment, the fourth assessment frequency is at least generally adjacent to a "zero slope" region of the baseline frequency response. In the event that the part-under-test has one or more surface defects, the corresponding SAW mode in the PUT frequency response may be compressed (compared to the first SAW mode in the baseline frequency response) and which may result in the development of one or more degenerate peaks at lower frequencies than the corresponding SAW mode. Therefore, the third assessment frequency in the PUT frequency response may be at a lower frequency than the first assessment frequency in the baseline frequency response.

Values for the third and fourth assessment frequencies may be derived such that the area of the PUT frequency response between the third and fourth assessment frequencies is the same predetermined percentage (as used above for the selection of the first and second assessment frequencies) of an area of the PUT frequency response over the reference frequency range (e.g., the third and fourth assessment frequencies may be selected for the PUT frequency response so that the corresponding area is the same size as the area between the first and second assessment frequencies for the baseline frequency response).

Satisfaction of the surface defect trigger condition may require that the second differential be at least a predetermined amount larger than the first differential (and which may be characterized as the first threshold). The surface defect trigger condition may be satisfied based solely on the existence of a single surface defect condition (e.g., where the second differential is at least a predetermined amount larger than the first differential for a single SAW mode, and where this predetermined amount may be the first threshold). However, the surface defect trigger condition could be configured so as to require that a predetermined number of multiple surface defect conditions exist in order for the surface defect trigger condition to be satisfied (e.g., the second differential may need to be at least a predetermined amount larger than the first differential for each of multiple SAW modes, and where this predetermined amount may be the first threshold).

A surface defect condition may be equated as existing when there is a predetermined relationship between the noted second differential (between the fourth and third assessment frequencies for the first SAW mode area associated with the PUT frequency response) and the noted first differential (between the second and first assessment frequencies for the baseline SAW mode area associated with the baseline frequency response). One or more surface defect conditions may be required to exist in order to satisfy the surface defect trigger condition. A surface defect condition may be equated with the second differential being at least 15% larger than the first differential in one embodiment, and with the second differential being at least 30% larger than the first differential in another embodiment. A surface defect condition may be equated with the first differential being no more than 70% of the second differential in one embodiment, and with the first differential being no more than 85% of the second differential in another embodiment.

A third aspect of the present invention is embodied by an evaluation of a part for the existence of one or more surface defects. First and second assessment frequencies that encompass a first surface acoustical wave (SAW) are identified in a baseline frequency response (e.g., a frequency response that is equated with an acceptable part). A reference frequency is selected that is between the first and second assessment frequencies in the baseline frequency response. A part-under-test is excited using at least one input frequency. The corresponding first SAW mode is identified in a frequency response of the part-under-test to this excitation (hereafter, a "part-under-test or PUT frequency response"). Values for third and fourth assessment frequencies within the PUT frequency response are derived so as to encompass the corresponding first SAW mode, and such that the area of the PUT frequency response between the third and fourth assessment frequencies is at least substantially equal to an area of the baseline frequency response between the first and second assessment frequencies. A comparison is made of the relationship between the reference frequency (previously selected in relation to the baseline frequency response) and each of the third and fourth assessment frequencies associated with the PUT frequency response. The part-under-test is characterized as being defective based upon satisfaction of a surface defect trigger condition. At least part of this surface defect trigger condition may be satisfied when a predetermined relationship is identified as existing in relation to the reference frequency and third assessment frequency, and in relation to the reference frequency and the fourth assessment frequency.

A number of feature refinements and additional features are applicable to the third aspect of the present invention. These feature refinements and additional features may be used individually or in any combination. The following discussion is applicable to the third aspect, up to the start of the discussion of a fourth aspect of the present invention.

The reference frequency may be selected such that a first area of the baseline frequency response (between the first assessment frequency and the reference frequency) is equal to a second area of the baseline frequency response (between the reference frequency and the second assessment frequency). Other reference frequencies may be appropriate. The first and second assessment frequencies (associated with the baseline frequency response) may be selected so as to include a SAW mode that corresponds to the first SAW mode in the PUT frequency response. In one embodiment, the first and second assessment frequencies are at least generally adjacent to a "zero slope" region of the baseline frequency response. In one embodiment, the first and second assessment frequencies at least generally define the boundaries of the first SAW mode.

The "predetermined relationship" between the reference frequency and each of the third and fourth assessment frequencies may compare two differentials in the case of the third aspect. At least part of the surface defect trigger condition may be satisfied when a first differential (between the reference frequency and the third assessment frequency; e.g., the reference frequency minus the third assessment frequency) is at least a predetermined amount larger than a second differential (between the fourth assessment frequency and the same reference frequency; e.g., the fourth assessment frequency minus the reference frequency). This may be characterized as the first differential satisfying a first threshold. In one embodiment, this first threshold is at least about 100% (e.g., the difference between the reference frequency and the third assessment frequency may be required to be at least twice as large as the difference between the fourth assessment frequency and the reference frequency in order to be equated with a surface defect condition). In one embodiment, this first threshold is at least about 150% (e.g., the difference between the reference frequency and the third assessment frequency may be required to be at least 2.5 times as large as the difference between the fourth assessment frequency and the reference frequency in order to be equated with a surface defect condition).

A surface defect condition may be equated as existing when there is a predetermined relationship between the noted second differential (between the fourth assessment frequency and the reference frequency) and the noted first differential (between the same reference frequency and the third assessment frequency). One or more surface defect conditions may be required to exist in order to satisfy the surface defect trigger condition. A surface defect condition may be equated with the first differential being at least 100% larger than the second differential in one embodiment, with the first differential being at least 150% larger than the second differential in another embodiment, with the first differential being at least 50% larger than the second differential in another embodiment, and with the first differential being at least 25% larger than the second differential in another embodiment. A surface defect condition may be equated with the second differential being no more than 50% of the first differential in one embodiment, and with the second differential being no more than 40% of the first differential in another embodiment.

A surface defect trigger condition may be satisfied based solely on the existence of a single surface defect condition (i.e., in relation to a single SAW mode); e.g., the first differential being at least a predetermined amount larger than the second differential for a single SAW mode in the PUT frequency response). However, the surface defect trigger condition could be configured so as to require that a predetermined number of multiple surface defect conditions exist in order for the surface defect trigger condition to be satisfied (e.g., a surface defect condition in accordance with the foregoing may be required to exist for a predetermined number of different SAW modes; the first differential being at least a predetermined amount larger than the second differential may be required for each of a plurality of different SAW modes in the PUT frequency response).

A fourth aspect of the present invention is embodied by an evaluation of a part for the existence of one or more surface defects. A part-under-test is excited using at least one input frequency. Both a first surface acoustical wave (SAW) and at least a degenerate peak are identified in a frequency response of the part-under-test to this excitation (hereafter, a "part-under-test or PUT frequency response"). An amplitude of this first SAW mode is compared with the amplitude of a degenerate peak. The part-under-test is characterized as being defective based upon an existence of a surface defect trigger condition. At least part of this surface defect trigger condition may be satisfied when a predetermined relationship exists between the amplitude of the first SAW mode and the amplitude of a degenerate peak.

A number of feature refinements and additional features are applicable to the fourth aspect of the present invention. These feature refinements and additional features may be used individually or in any combination. The following discussion is applicable to at least this fourth aspect.

The comparison of the amplitude of the first SAW mode to the amplitude of a degenerate peak may entail comparing a first threshold to the ratio of the first SAW mode amplitude to the degenerate peak amplitude. A surface defect condition may be equated with this ratio satisfying a first threshold. A surface defect condition may be equated with this ratio being no larger than a predetermined value (e.g., a first threshold).

A surface defect condition may be equated as existing when there is a predetermined relationship between the amplitude of the first SAW mode and the amplitude of a degenerate peak. One or more surface defect conditions may be required to exist in order to satisfy the surface defect trigger condition. A surface defect condition may be equated as existing when the amplitude of the first SAW mode, divided by the amplitude of a degenerate peak, is no more than about 8 in one embodiment, and is no more than about 4 in another embodiment. A surface defect condition may be equated as existing when the amplitude of a degenerate peak, divided by the amplitude of the first SAW mode, is at least about 12% in one embodiment, and is at least about 25% in another embodiment.

An assessment ratio may be calculated, where this assessment ratio is the first SAW mode amplitude, divided by the degenerate peak amplitude. The assessment of the part-under-test for a defective condition may entail comparing this assessment ratio to at least first and second defect grades. A defect in the first defect grade may be a smaller defect than a defect in the second defect grade. The first defect grade may include a first range of values, and the second defect grade may include a second range of values, with the first and second defect grades having no overlapping values.

The surface defect trigger condition may be satisfied based solely on there being a predetermined relationship between the amplitude of the first SAW mode and the amplitude of one degenerate peak (e.g., a degenerate peak between the first SAW mode and an adjacent SAW mode). The surface defect trigger condition may require that there be a predetermined relationship between the amplitude of the first SAW mode and the amplitude of two or more degenerate peaks (e.g., two or more degenerate peaks between the first SAW mode and an adjacent SAW mode). The surface defect trigger condition could require that there be a predetermined relationship between the amplitude of the first SAW mode and the amplitude of one or more degenerate peaks (e.g., one or more degenerate peaks between the first SAW mode and an adjacent SAW mode), as well as that there be a predetermined relationship between the amplitude of at least one other SAW mode and the amplitude of one or more degenerate peaks (e.g., one or more degenerate peaks between the corresponding SAW mode and an adjacent SAW mode).

A number of feature refinements and additional features are separately applicable to each of above-noted first, second, third, and fourth aspects of the present invention. These feature refinements and additional features may be used individually or in any combination in relation to each of the first, second, third, and fourth aspects. The present invention may be used to determine whether the part-under-test includes at least one surface defect (the present invention does not require that the number and/or location of one or more surface defects be identified). The part-under-test for purposes of the present invention may be of a symmetrical configuration. Representative configurations for a part-under-test for purposes of the present invention include without limitation a ball, sphere, cylinder, tapered roller, right circular cylinder, and the like.

The part-under-test may be characterized as being defective based upon satisfaction of a surface defect condition. One or more surface defect conditions (e.g., a predetermined number) may be required to exist in order to satisfy a given surface defect trigger condition. It should be appreciated that the existence of a "surface defect condition" may not necessarily be indicative of the actual number of surface defects in a part-under-test. The existence of a single "surface defect condition" could exist when there is only a single surface defect in a given part-under-test. The existence of a single "surface defect condition" could exist when there are multiple surface defects in a given part-under-test. A single surface defect could produce surface defect conditions at each of multiple SAW modes.

A frequency response may be in the form of a plot of a collection of responses of the part-under-test at each frequency that may be used to drive the part-under-test. For instance, if the part-under-test is driven at frequency $f_1$, the amplitude of the response of the part-under-test at this same frequency $f_1$ may be included in the noted plot at the frequency $f_1$; if the part-under-test is driven at frequency $f_2$, the amplitude of the response of the part-under-test at this same frequency $f_2$ may be included in the plot at the frequency $f_2$; if the part-under-test is driven at frequency $f_3$, the amplitude of the response of the part-under-test at this same frequency $f_3$ may be included in the plot at this frequency $f_3$; and so forth. Any such plot is within the scope of a "frequency response" as set forth herein.

A surface acoustical wave (SAW) mode may be identified in a frequency response (to the excitation of the part-under-test) in any appropriate manner in relation to the present invention. The frequency at which a given SAW mode should appear may be determined mathematically. Another option is to determine the interval between SAW modes at a particular input frequency to a part, and to use this information to identify the SAW mode(s) of interest in the frequency response to the excitation of the part-under-test.

Original equipment manufacturer or OEM parts may be evaluated using the present invention. Non-OEM parts may also be evaluated using the present invention, for instance for purposes of determining whether a non-OEM part complies with an OEM part or other control group (of one or more other parts and/or part specifications).

The part-under-test may be in the form of an in-service part. An in-service part may be characterized as a part that has been released from production for use in one or more end-use applications. An "in-service part" in the context of the present invention encompasses a part that has been used to at least some extent after having been released by the manufacturer. An in-service part may be a part that has been put into use by a party other than the manufacturer (e.g., a customer or end user). Although an in-service part could be used autonomously or independently of any other parts, an in-service part may be incorporated by an appropriate assembly or system (e.g., a turbine blade (an in-service part) in a jet engine (an assembly or system)).

The present invention may be used to evaluate new production parts (e.g., the part-under-test may be a new production part). A new production part may be characterized as a newly manufactured part that has not yet been released from production (e.g., parts that have not yet been shipped for use by an end user or customer). New production parts include parts that may have undergone at least some post-production testing of any appropriate type (including without limitation a surface defect inspection in accordance with the present invention and/or a resonance inspection).

The various aspects of the present invention each may be implemented as a method and/or as an inspection system or tool. In the case of an inspection system or tool, a surface defect assessment module may be configured to execute the assessments noted herein (e.g., such a surface defect assessment module may be configured to identify reference peaks and/or SAW modes in the frequency response, to assess one or more zones for the existence of one or more degenerate peak conditions, and/or to assess for the existence/satisfaction of a surface defect trigger condition), and the part-under-test may be excited and the frequency response may be obtained in accordance with any one or more of the following configurations.

An inspection of the part-under-test for purposes of the present invention may utilize a first transducer that excites or drives the part-under-test at multiple frequencies (e.g., by sweeping through a predetermined range of frequencies in any appropriate manner), along with at least one other transducer that measures the frequency response of this part-under-test to such excitations or drive frequencies (e.g., thereby encompassing using two "receiver" transducers). Any number of frequencies may be used to excite the part-under-test for the inspection, and the excitation frequencies may be input to the part-under-test in any appropriate pattern and for any appropriate duration. Another option is to use a single transducer for performing an inspection of the part-under-test. In this case, a transducer may drive the part-under-test at a certain frequency for a certain amount of time, and thereafter this same transducer may be used to obtain the frequency response of the part-under-test (e.g., after terminating the driving of the transducer at an input frequency). This may be repeated for multiple input or drive frequencies.

Any appropriate combination of excitation or drive frequencies may be used for an inspection in accordance with the present invention. Each transducer that is used to perform an inspection may be of any appropriate size, shape, configuration, and/or type. Although an inspection in accordance with the present invention could possibly be performed in situ (e.g., with the part in an installed condition or state), such an inspection will more typically be performed prior to installing a part for its end-use application or with the part being in an uninstalled condition or state.

An inspection of the part-under-test in accordance with the present invention may include using at least one transducer that excites the part-under-test through a range of frequencies, and using at least two other transducers to measure the frequency response of the part-under-test. Another option for an inspection of the part-under-test is to use a first transducer that excites the part-under-test at a number of different frequencies, and using this same transducer to measure the frequency response of the part-under-test.

An inspection in accordance with the present invention may include exciting the part-under-test using at least one drive transducer that is in contact with the part-under-test. Another option for an inspection in the case of the present invention is to excite the part-under-test using at least one drive transducer that is maintained in spaced relation to the part-under-test throughout the inspection. In one embodiment, such a drive transducer (e.g., a drive transducer that is spaced from the part-under-test for the inspection) may be in the form of a laser.

An inspection of the part-under-test in accordance with the present invention may entail obtaining a frequency response of this part using at least one receive transducer that is in contact with the part-under-test. Another option for this inspection is to obtain a frequency response of the part-under-test using at least one receive transducer that is maintained in spaced relation to this part-under-test. In one embodiment, a receive transducer used in the inspection of the part-under-test is in the form of a laser. The inspection of the part-under-test may include obtaining a frequency response of this part-under-test using laser vibrometry. The frequency response of the part-under-test in this case may be obtained from a single location using laser vibrometry. Another option for this case is to obtain the frequency response of the part-under-test by laser scanning multiple locations on the surface of this part-under-test.

Any feature of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a resonance inspection system utilizes "a frequency response transducer" alone does not mean that the resonance inspection system utilizes only a single frequency response transducer). Moreover, any failure to use phrases such as "at least one" also does not limit the corresponding feature to the singular (e.g., indicating that a resonance inspection system utilizes "a frequency response transducer" alone does not mean that the resonance inspection system utilizes only a single frequency response transducer). Use of the phrase "at least generally" or the like in relation to a particular feature encompasses the corresponding characteristic and insubstantial variations thereof (e.g., indicating that a structure is at least generally cylindrical encompasses the structure being cylindrical). Finally, a reference of a feature in conjunction with the phrase "in one embodiment" does not limit the use of the feature to a single embodiment.

DETAILED DESCRIPTION

Various applications of resonance inspection (e.g., resonance ultrasound spectroscopy; process compensated resonance testing) are addressed herein. Various principles that may relate to resonance inspection are addressed in the following U.S. patents, the entire disclosures of which are incorporated by reference in their entirety herein: U.S. Pat. Nos. 5,408,880; 5,425,272; 5,495,763; 5,631,423; 5,641,905; 5,837,896; 5,866,263; 5,952,576; 5,965,817; 5,992,234; and 6,199,431.

Figure 1:
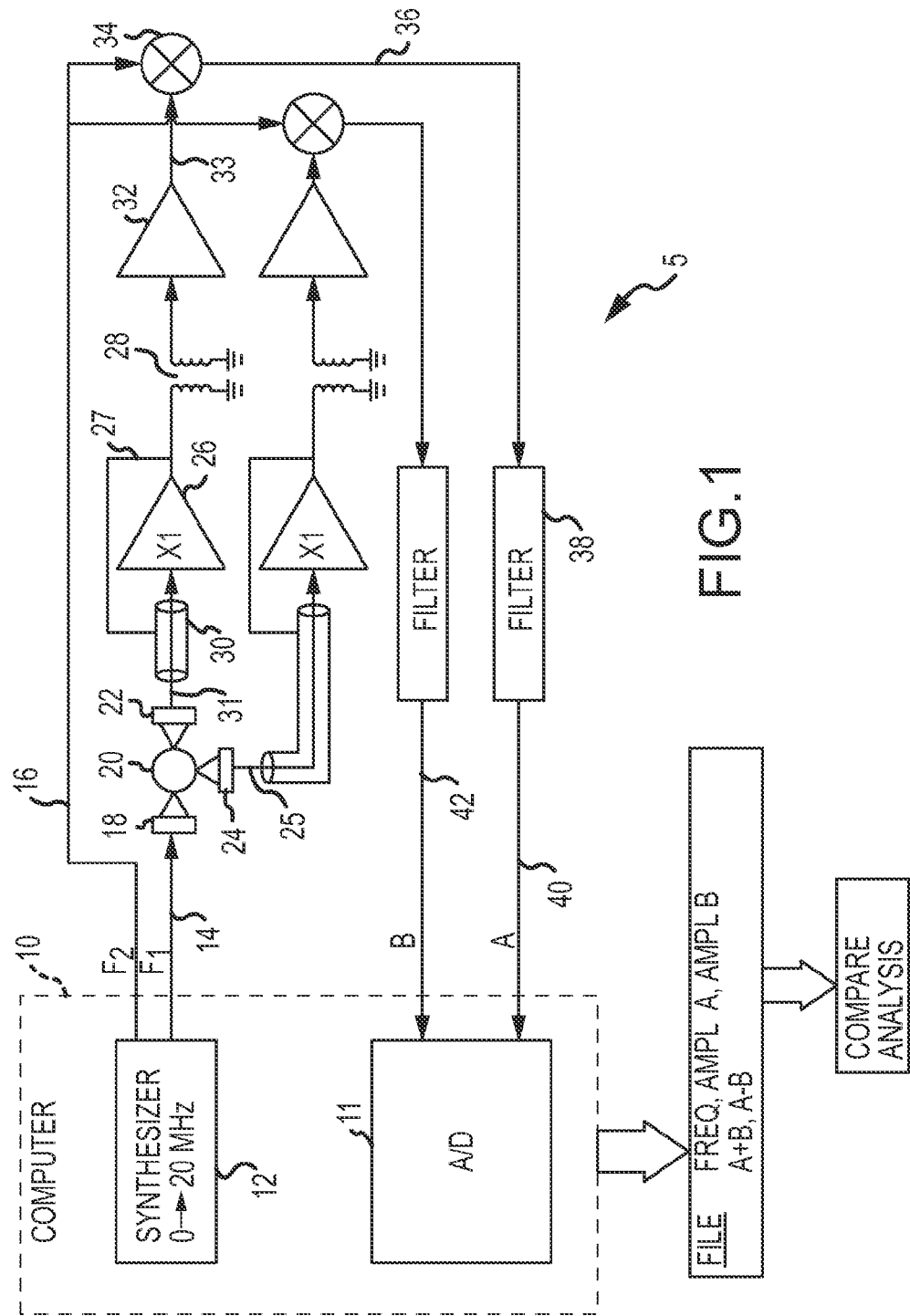
FIG. 1 is a block-diagram of one embodiment of a resonance inspection tool.
Figure 2:
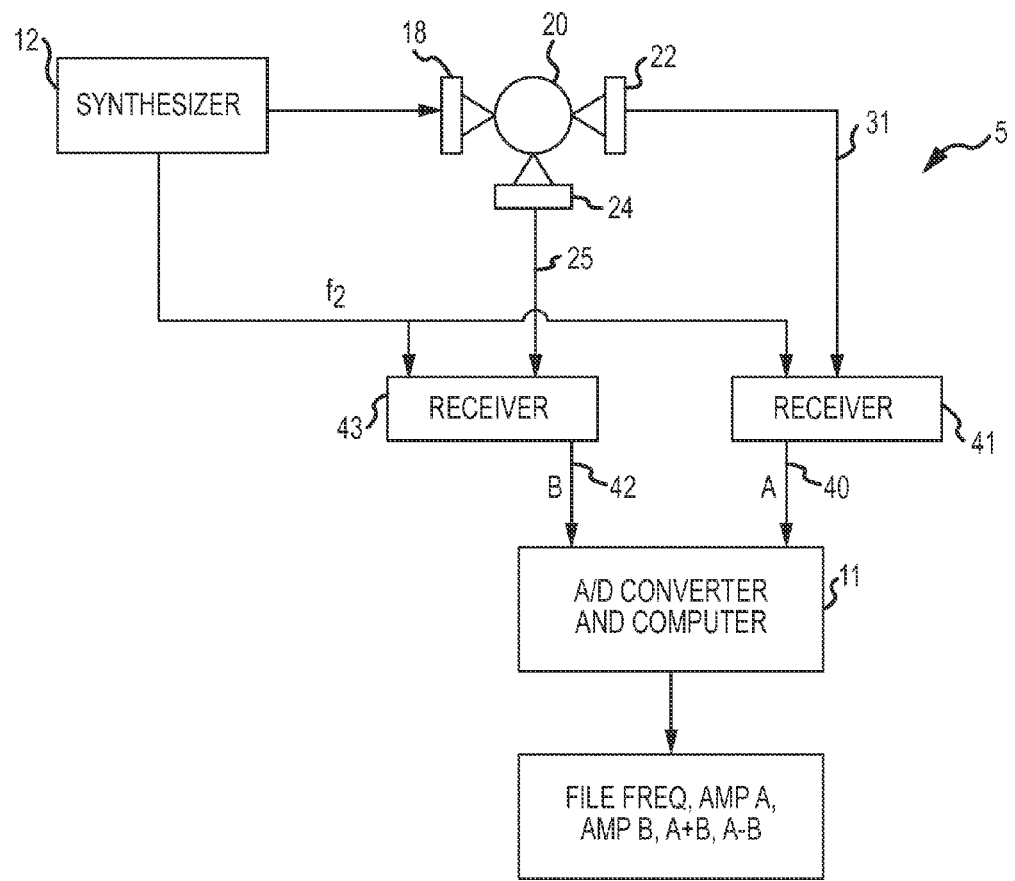
FIG. 2 shows a simplified block diagram of the resonance inspection tool of FIG. 1.

One embodiment of a resonance inspection tool or system (e.g., for accommodating resonant ultrasound spectroscopy measurement with a plurality of sensors; for process compensated resonance testing) is illustrated in FIGS. 1 and 2, and is identified by reference numeral 5. The resonance inspection tool 5 includes a computer 10 that provides for control of a synthesizer 12 and an analog to digital converter 11 for each data input channel connected to each receiving or response transducer 22, 24 of the resonance inspection tool 5. Transducer 22 has an output on line 31, while transducer 24 has an output on line 25.

Synthesizer 12 may have a frequency range from greater than 0 to 20 M Hertz. Other frequency ranges may be appropriate. Synthesizer 12 provides two outputs which are the frequency F1 at output 14 and a second output which is the frequency F2 at line 16. In one embodiment, the frequency F2 is either F1 plus a constant frequency such as 1000 Hertz for heterodyne operation of the receiver, or at F1 for homodyne operation. A first transducer 18 (e.g., the input or driving transducer) is excited at a frequency F1 by synthesizer 12. Transducer 18 provides vibration (e.g., ultrasonic) to an object 20 to be tested via resonance inspection.

The response of the object 20 is then received by two separate output transducers 22 and 24. The circuitry from the output transducer 22 and A/D converter 11 can be identical to circuitry between output transducer 24 and A/D converter 11. For this reason, only the circuitry between output transducer 22 and A/D converter 11 will be discussed below. The times one (.times.1) amplifier 26 is connected to the output transducer 22, provides current for transformer 28, and has a feedback 27.

The output of transducer 22 is connected to a receiver 41 (FIG. 2). Receiver 41 is used for the purpose of providing amplification and noise rejection in the circuit between output transducer 22 and A/D converter 11. The output A (line 40) is applied to the A/D converter 11 within the computer 10. The A/D converter 11 provides an ND conversion for each of lines 40 and 42. The converted information is then entered into a file which consists of the measured frequency, the amplitude of A, the amplitude of B, the amplitude of A plus B, and the amplitude of A minus B. This file is then used for further analysis of the spectrum to determine characteristics of a part 20 being tested.

The times one (.times.1) amplifier 26 provides feedback to an inner coaxial cable shield 30 which surround the lead from transducer 22 to amplifier 26. Shield 30 is another grounded shield which can also be used for noise suppression. The outer surrounding coaxial cable is not shown in FIG. 1. If lead 31 is short, the shield 30 may be omitted because capacitance will not be too large. The purpose of the inner shield 30 is to provide a cancellation of capacitance of the lead 31.

The transformer 28 may be a 4:1 step-down transformer used for impedance matching to the input of amplifier 32. In this regard, it should be noted that the output impedance of amplifier 26 may be much lower than the output impedance of transducer 22. This provides for the power gain and the necessary feedback to shield 30. The amplifier 32 may have a gain factor of 100:1 or a 40 db gain. Other gain factors may be appropriate. The amplifier 26 may be a broad-band amplifier having a band pass on the order of 50 M Hertz.

Mixer 34 has an output signal (e.g., a 1 K Hertz signal) having a magnitude which is proportional to the magnitude of the frequency F1 provided on line 14 from synthesizer 12. The function of the synthesizer 12 is to provide a point-by-point multiplication of instantaneous values of inputs on lines 16 and 33. The mixer 34 also has many high frequency output components which are of no interest. The high frequency components are therefore filtered out by the low-band pass filter 38 which is connected to mixer 34 by line 36. Filter 38 serves to clean-up the signal from mixer 34 and provide a voltage on line 40 which is only the output signal at an amplitude which is proportional to the amplitude of the output 31 of transducer 22.

Operation of the resonance inspection tool 5 will be briefly described in relation to measurement steps performed by measurement of the output of either transducer 22 or transducer 24 controlled by computer 10. A measurement cycle may be initiated, and provides initialization for the frequency F and the desired frequency step. The frequency step may be 1 Hertz or any other frequency selected for the measurement. Although a constant frequency step may be utilized, the frequency step may be determined by any appropriate algorithm. In one embodiment, the frequency step is determined by determining the start frequency and the stop frequency, and dividing the frequency difference by the number of steps desired for the measurement. In any case, the synthesizer 12 is configured to provide a plurality of input or drive frequencies to transducer 18.

Once a signal is picked up by the receiver (i.e., an output on line 33), a pause for ring delay there is a provided. The pause for ring delay may be on the order of 30 milliseconds, although other ring delays can be used if the object under test 20 has resonances that are narrower than a few Hertz. The purpose of the pause is to give the object 20 an opportunity to reach its steady state magnitude in response to a steady input from transducer 18. The pause time is time after the frequency is applied and before detection is initiated.

After the ring delay is complete, analog-to-digital converter 11 provides an output that can be used by the data recording computer. The output of the A/D conversion is then written to a file by the computer 10 for the purpose of analysis of the data by another program. Data comprising the unique signature or characterizing of the object 20 is written into file as it is created. Reading may be stopped when a read frequency is present and step 66 stops the program. Once information is entered into file, subsequent processing can be used to generate a signature or characterize the object 20 such as the resonant magnitudes, the sum of resonant magnitudes, the difference of resonant magnitudes, or other manipulations of the multiple channel multiple frequency measurement which is used to perform the unique signature of the object 20. The magnitude of the outputs at each sensor location for each resonance frequency may be compared.

Figure 3:
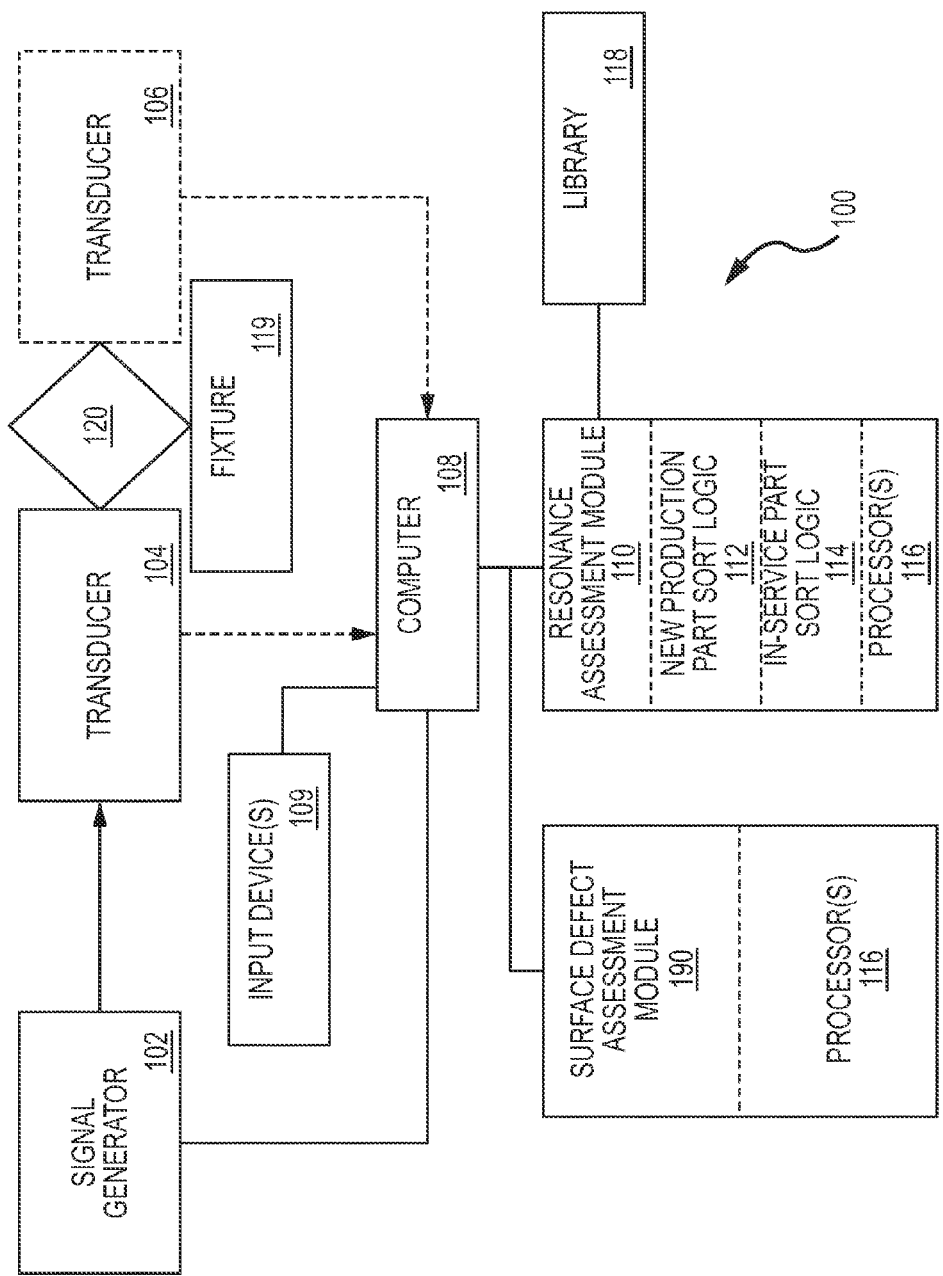
FIG. 3 is a block-diagram of one embodiment of an inspection tool that accommodates both a resonance inspection and a surface defect inspection.

Another embodiment of an inspection tool or system is illustrated in FIG. 3 and is identified by reference numeral 100. The inspection tool 100 may be used to assess a part or part-under-test (PUT) 120. This part-under-test 120 may be retained in a fixture 119 in any appropriate manner for execution of one or more inspections. Two different types of inspections may be undertaken using the configuration of the tool 100 shown in FIG. 3. The tool 100 may include a resonance assessment module 110 for performing a resonance inspection of the PUT 120. The tool 100 may include a surface defect assessment module 190 for performing a surface inspection of the PUT 120. Either one or both of these modules 110, 190 may be utilized by the tool 100. Both modules 110, 190 may entail driving the PUT 120 at one or more input frequencies and then assessing the frequency response of the PUT 120. The surface defect assessment module 190 may be used to identify only surface defects in the PUT 120. The resonance assessment module 110 may be used to identify at least the existence of defects anywhere within the PUT 120.

The inspection tool 100 includes a signal generator 102 of any appropriate type, at least one transducer (e.g., transducer 104), and a computer 108. The transducer 104 may be of any appropriate type. In one embodiment, the transducer 104 is in physical contact with the PUT 120 to acquire data for the inspection of the PUT 120, and in this case may be characterized as being part of the fixture 119 for the PUT 120. Another embodiment has the transducer 104 being maintained in spaced relation to the PUT 120 to acquire data for the inspection of the PUT 120 (e.g., a laser, such as Nd:YAG lasers, TEA $CO_2$ lasers, excimer lasers, or diode lasers).

A PUT 120 that is analyzed or assessed by the inspection tool 100 may be of any appropriate size, shape, configuration, type, and/or class. For purposes of the inspection tool 100, there could be two part classes. One part class includes new production parts—newly manufactured parts that have not yet been released from production (e.g., parts that have not been shipped for use by an end user or customer). New production parts include parts that may have undergone at least some post-production testing of any appropriate type (including without limitation a resonance inspection). Another part class includes in-service parts—parts that have been released from production for use in one or more end-use applications. An "in-service part" in the context of the embodiments to be addressed herein encompasses a part that has been used to at least some extent after having been released by the manufacturer. An in-service part may be a part that has been put into use by a party other than the manufacturer (e.g., a customer or end user). Although an in-service part could be used autonomously or independently of any other parts, an in-service part also may be incorporated by an assembly or system (e.g., a turbine blade (an in-service part) in a jet engine (an assembly or system)).

The signal generator 102 generates signals that are directed to the transducer 104 for transmission to the PUT 120 in any appropriate manner/fashion (e.g., via physical contact between the transducer 104 and the PUT 120; through a space between the transducer 104 and the PUT 120). Signals provided to the transducer 104 by the signal generator 102 are used to mechanically excite the PUT 120 (e.g., to provide energy to the PUT 120 for purposes of inducing vibration). Multiple frequencies may be input to the PUT 120 through the transducer 104 in any appropriate manner. This may be characterized as "sweeping" through a range of frequencies that are each input to the PUT 120, and this may be done in any appropriate manner for purposes of the inspection tool 100. Any appropriate number/range of frequencies may be utilized, and any appropriate way of progressing through a plurality of frequencies (e.g., a frequency range) may be utilized by the inspection tool 100.

In one embodiment, at least one other transducer 106 is utilized in the inspection of the part PUT using the inspection tool 100 of FIG. 3, including where two transducers 106 are utilized (e.g., in accordance with the embodiment of FIGS. 1 and 2 noted above). Each of the transducers 106, as well as the input or drive transducer 104, may be in physical contact with the PUT 120. It may be such that the PUT 120 is in fact entirely supported by the transducer 104 and any additional transducers 106 (e.g., the drive transducer 104 and one or more receive transducers 106 may define the fixture 119). Each transducer 106 that is utilized by the inspection tool 100 is used to acquire the frequency response of the PUT 120 to the frequencies input to the PUT 120 by the drive transducer 104, and therefore each transducer 106 may be characterized as an output or receiver transducer 106.

One or more transducers 106 utilized by the inspection tool 100 may be maintained in physical contact with the part 120 throughout the acquisition of data for an inspection. Another option is for one or more of the transducers 106 to be maintained in spaced relation with the part 120 throughout the acquisition of data for an inspection. A transducer 106 in the form of a laser may be maintained in spaced relation with the part throughout the acquisition of data for an inspection, and may be utilized to obtain the frequency response of the PUT 120. Representative lasers that may be utilized as a transducer 106 by the inspection system 100 include without limitation Nd:YAG lasers, TEA $CO_2$ lasers, excimer lasers, or diode lasers. In one embodiment, the frequency response of the PUT 120 is acquired by laser vibrometry utilizing at least one transducer 106. A given transducer 106 in the form of a laser may acquire data on the PUT 120 from a single location, or a given transducer 106 in the form of a laser could acquire data on the PUT 120 by scanning the laser over multiple locations on the PUT 120.

Another embodiment of the inspection tool 100 of FIG. 3 utilizes only the transducer 104. That is, no additional transducers 106 are utilized by the inspection tool 100 in this case, and therefore the transducer 106 is presented by dashed lines in FIG. 3. In this case, the transducer 104 is used to input a drive signal to the PUT 120 (e.g., to excite the PUT 120 at a plurality of different frequencies), and is also used to acquire the frequency response of the PUT 120 to these input drive frequencies. Representative configurations for this drive/receive transducer configuration 104 include without limitation piezoceramic, piezocomposites, piezoelectric quartz crystal, and other electromechanical materials.

In the above-noted drive/receive transducer configuration, a first drive signal at a first frequency (from the signal generator 102) may be transmitted to the PUT 120 through the transducer 104, the transmission of this first drive signal may be terminated, and the transducer 104 may be used to acquire a first frequency response of the PUT 120 to this first drive signal (including while a drive signal is being transmitted to the PUT 120). The signal generator 102 may also be used provide a second drive signal at a second frequency to the transducer 104, which in turn transmits the second drive signal to the PUT 120, the transmission of this second drive signal may be terminated, and the transducer 104 may once again be used to acquire a second frequency response of the PUT 120 to this second drive signal (including while a drive signal is being transmitted to the PUT 120). This may be repeated any appropriate number of times and utilizing any appropriate number of frequencies and frequency values. One or more drive signals may be sequentially transmitted to the PUT 120 by the signal generator 102 and transducer 104, one or more drive signals may be simultaneously transmitted to the PUT 120 by the signal generator 102 and transducer 104, or any combination thereof.

The frequency response of the PUT 120 is transmitted to the computer 108 of the inspection tool 100 of FIG. 3. This computer 108 may be of any appropriate type and/or configuration, and is used by the inspection tool 100 to evaluate the part 120 in at least some fashion (e.g., to determine whether to accept or reject the part 120). The computer 108 may include one or more data input devices 109 of any appropriate type (e.g., keyboard, mouse, touch screen).

Generally, the part 120 is vibrated by the transducer 104 according to a predetermined signal(s), and the PUT 120 is evaluated by the resulting vibrational (e.g., whole body) response of the part 120 in the case of a resonance inspection. For instance, this evaluation may entail assessing the part 120 for one or more defects of various types, assessing whether the part 120 is at or near the end of its useful, life, assessing whether the part 120 is aging normally or abnormally, or any combination thereof. In any case, the resonance assessment module 110 may be configured to evaluate the results of a resonance inspection, for instance for purposes of determining whether the PUT 120 should be accepted or rejected by the inspection tool 100, determining whether the PUT 120 is at an end-of-life state or condition, or the like. A PUT 120 that is "accepted" by the inspection tool 100 from a resonance inspection may mean that the inspection tool 100 has determined that the part 120 may be put into service (e.g., utilized for its intended purpose(s) and/or used according to its design specifications). In one embodiment, a PUT 120 that has been accepted by the inspection tool 100 from a resonance inspection means that the tool 100 has determined that the PUT 120 is free of defects, is not in an end-of-life condition or state, is aging normally, or any combination thereof. A PUT 120 that is "rejected" by the inspection tool 100 from a resonance inspection may mean that the inspection tool 100 has determined that the PUT 120 should not be put into service (e.g., should not be utilized for its intended purpose(s) and/or should no longer be used according to its design specifications). In one embodiment, a part 120 that has been rejected by the inspection tool 100 means that the tool 100 has determined that the part 120 includes at least one defect, is at or near an end-of-life condition or state, is aging abnormally, or any combination thereof.

The computer 108 may incorporate and utilize the above-noted resonance assessment module 110 to evaluate the response of the PUT 120 to a resonance inspection. The resonance assessment module 110 may be of any appropriate configuration and may be implemented in any appropriate manner. In one embodiment, the resonance assessment module 110 includes at least one new production part sort logic 112 (e.g., logic configured to determine whether to accept or reject new production parts), at least one in-service part sort logic 114 (e.g., logic configured to determine whether to accept or reject in-service parts), along with one or more processors 116 of any appropriate type and which may be implemented in any appropriate processing architecture. The assessment of the response of the PUT 120 to the input drive signals may entail comparing the response to a library 118 utilized by the inspection tool 100. This library 118 may be stored on a computer-readable storage medium of any appropriate type or types, including without limitation by using one or more data storage devices of any appropriate type and utilizing any appropriate data storage architecture.

Figure 4:
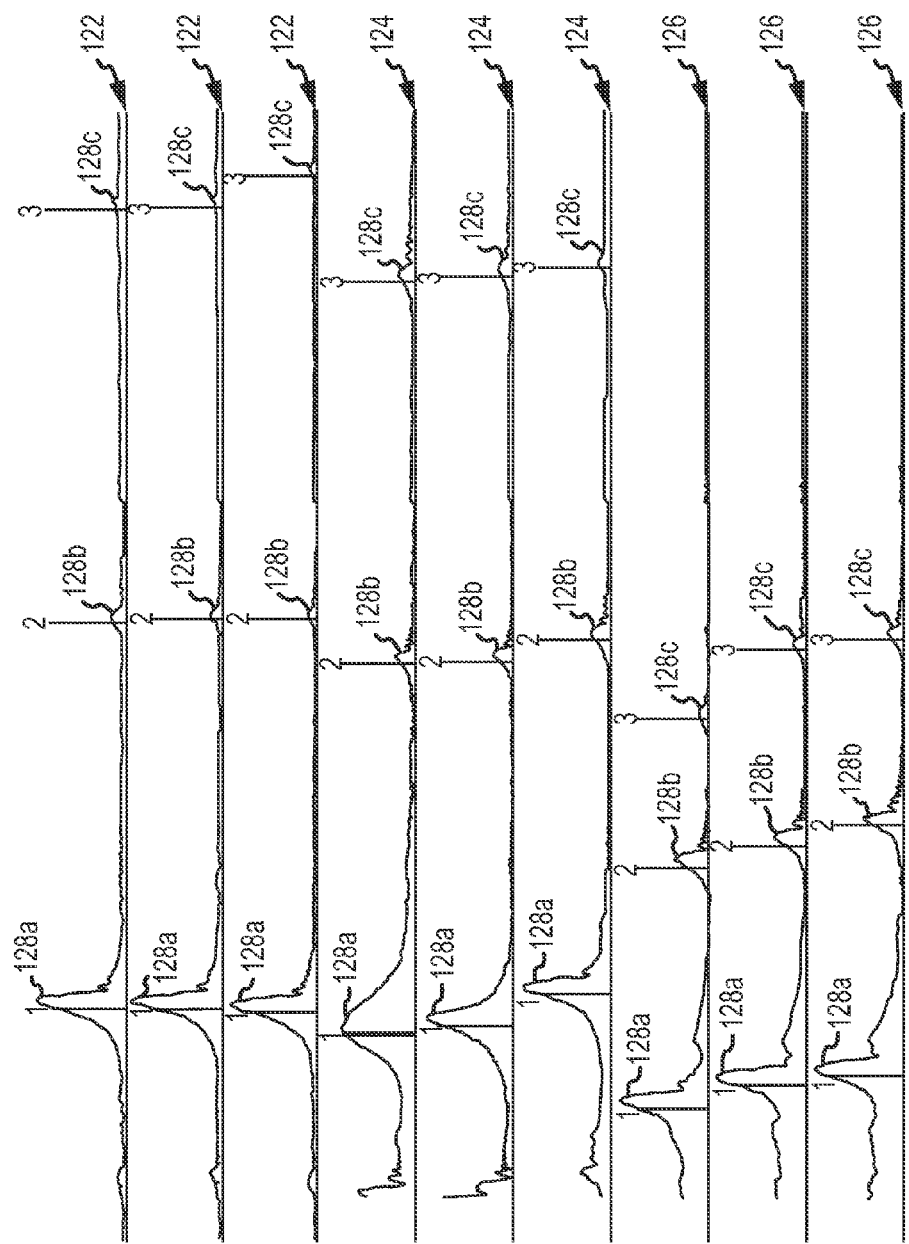
FIG. 4 presents various resonance inspection results of parts that may be included in a library utilized for conducting a resonance inspection with the inspection tool of FIG. 3.

The library 118 of the inspection tool 100 may include various types of resonance inspection results to allow the inspection tool 100 to assess a PUT 120. Generally, the resonance inspection results from the PUT 120 are compared with data in the library 118 from at least one other part that is the same as the PUT 120 in one or more respects (e.g., a PUT 120 in the form of a turbine blade will be compared to turbine blade data in the library 118; a PUT 120 in the form of a turbine blade will not be compared with ball bearing data in the library 118). Representative resonance inspection results are presented in FIG. 4, and are of a type that may be included in the library 118. The three spectra 122 shown in FIG. 4 represent the frequency response of a new production part 120 to a certain input frequency, and where this new production part 120 has been accepted by the inspection tool 100. Note how the three peaks 128*a*, 128*b*, and 128*c* differ in at least one respect between the various spectra 122, but yet the corresponding new production part 120 is acceptable in all three instances.

The three spectra 124 shown in FIG. 4 represent the frequency response of an in-service production part 120 to a certain input frequency, and where this in-service part 120 has been accepted by the inspection tool 100. Note how the three peaks 128*a*, 128*b*, and 128*c* in the spectra 124 differ in at least one respect from the corresponding peaks 128*a*, 128*b*, and 128*c* in the spectra 122 (again, associated with a new production part 120). The three spectra 126 shown in FIG. 4 represent the frequency response of an in-service production part 120 to a certain input frequency, and where this in-service part 120 has been rejected by the inspection tool 100. Note how the three peaks 128*a*, 128*b*, and 128*c* in the spectra 126 differ in at least one respect from the corresponding peaks 128*a*, 128*b*, and 128*c* in the spectra 124 (again, associated with an in-service part 120 that the inspection tool 100 would accept). Generally, each of the peaks 128*a*, 128*b*, and 128*c* in the spectra 126 has shifted to the left compared to the corresponding peaks 128*a*, 128*b*, and 128*c* in the spectra 122 and 124. Moreover, note the "compression" between the peaks 128*a*, 128*b* in the spectra 126 compared to the spectra 122, 124, as well as the "compression" between the peaks 128*b*, 128*c* in the spectra 126 compared to the spectra 122, 124.

Figure 5:
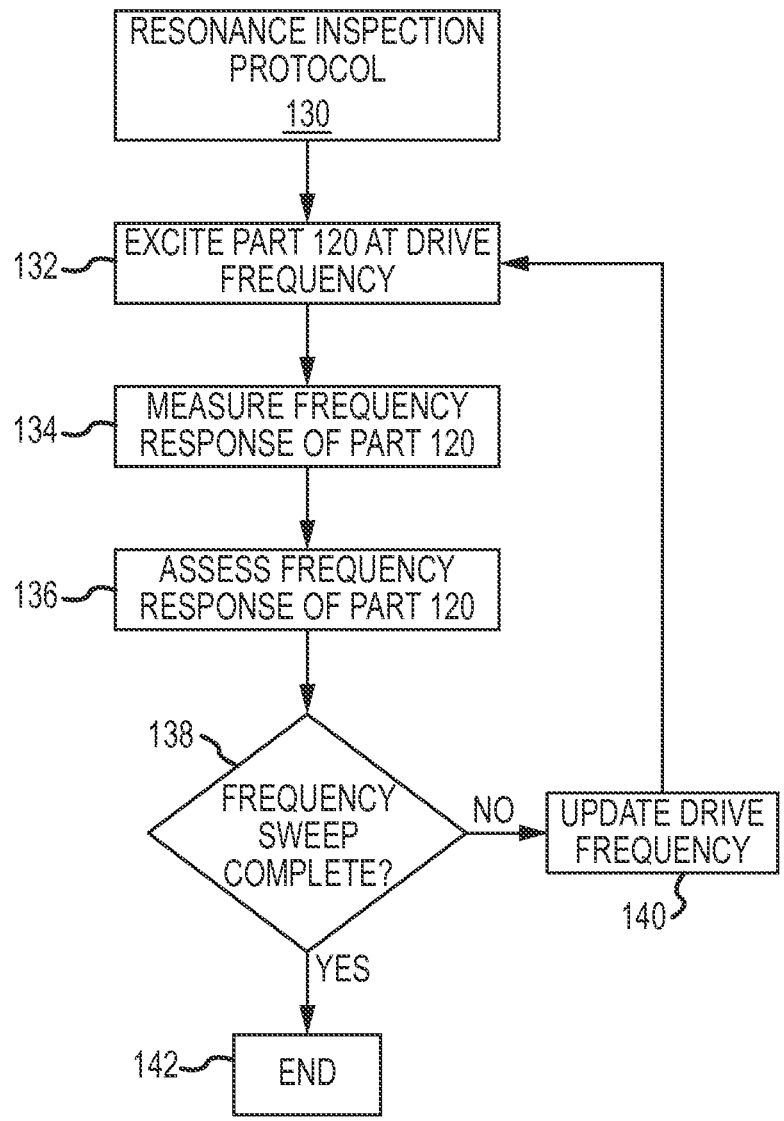
FIG. 5 is one embodiment of a resonance inspection protocol that may be utilized for conducting a resonance inspection with the inspection tool of FIG. 3.

One embodiment of a resonance inspection protocol that may be utilized by the inspection tool 100 of FIG. 3 is presented in FIG. 5 and is identified by reference numeral 130. Step 132 of the resonance inspection protocol 130 is directed to exciting a part 120 at a drive frequency (e.g. via a signal from the signal generator 102 that is input to the part 120 through the transducer 104). The response of the part 120 is obtained or measured pursuant to step 134 (e.g., via one or more transducers 106; via the transducer 104 in a single transducer configuration). It should be appreciated that steps 132 and 134 may be executed in at least partially overlapping relation (e.g., the frequency response of the part 120 could be obtained as a drive signal is being applied to the part 120), although steps 132 and 134 could be sequentially executed as well.

The frequency response of the part 120 is assessed pursuant to step 136 of the resonance inspection protocol 130. Step 138 of the protocol 130 is directed to determining if the frequency sweep is complete—whether each of the desired drive frequencies has been input to the part 120. If not, the protocol 130 proceeds to step 140, and which is directed to updating or changing the drive frequency to be input to the part 120. Control is then returned to step 132 of the protocol 130 for repetition in accordance with the foregoing. Once the part 120 has been driven at each of the desired frequencies, the protocol 130 may be terminated pursuant to step 142.

Step 136 of the resonance inspection protocol 130 is again directed to assessing the response (e.g., frequency; whole body) of the part 120 (e.g., using the sort logic 112 or 114 and/or comparing the response of the part 120 to the library 118 of the inspection tool 100). This assessment may be undertaken at any appropriate time and in any appropriate manner. For instance, the assessment associated with step 136 could be undertaken while the part 120 continues to be driven by a signal at one or more frequencies. Another option is for the assessment provided by step 136 to be undertaken only after all drive signals have been input to the part 120 (step 132), after the all frequency responses have been obtained (step 134), or both.

Figure 6:
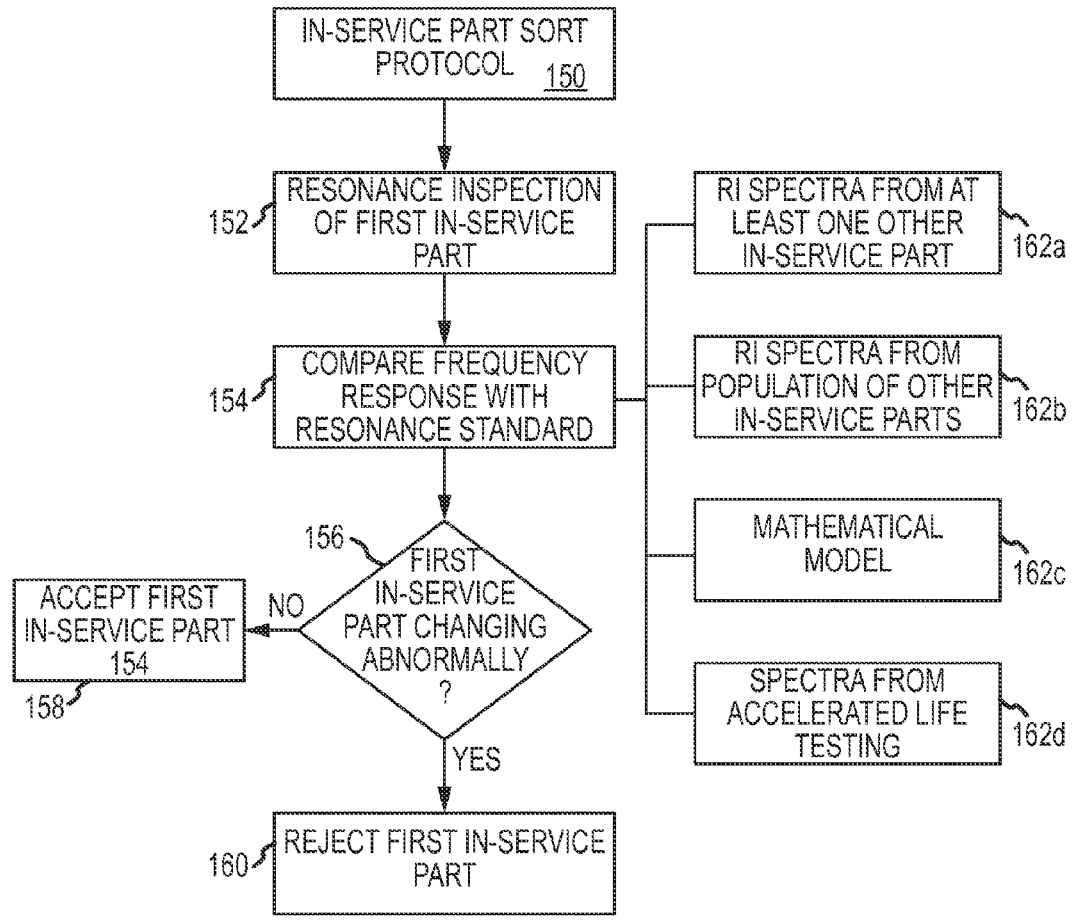
FIG. 6 is one embodiment of a sort protocol for in-service parts that may be utilized for conducting a resonance inspection with the inspection tool of FIG. 3.

One embodiment of a sort protocol for in-service parts is presented in FIG. 6 and is identified by reference numeral 150. The sort protocol 150 may be utilized by the in-service part sort logic 114 of the inspection tool 100 shown in FIG. 3, and is configured for the assessment of in-service parts. Generally, the sort protocol 150 is directed to determining whether or not an in-service part is experiencing normal changes while in service. Stated another way, the sort protocol 150 may be characterized as being directed to determining whether an in-service part is aging normally or abnormally and via a resonance inspection. Each resonance inspection of an in-service part may be conducted while the in-service part remains in an installed state or condition (e.g., in situ) for purposes of the sort protocol 150. Alternatively, each resonance inspection of an in-service part may be conducted with the in-service part being in an uninstalled state or condition (e.g., after having been removed from an assembly incorporating the same) for purposes of the sort protocol 150.

A resonance inspection of a first in-service part (e.g., part 120 shown in FIG. 3) is conducted pursuant to step 152 of the sort protocol 150 of FIG. 6 (e.g., via execution of the resonance inspection protocol 130 of FIG. 5). The frequency response of the first in-service part is compared with a resonance standard pursuant to step 154. This "resonance standard" may be incorporated by the library 118 used by the inspection tool 100 (FIG. 3) and/or may be utilized by the in-service part sort logic 114, and in any case may characterize or define what should be a "normal change" for a predetermined in-service part (e.g., to determine whether the first in-service part is changing or aging in a normal manner or fashion). That is, the comparison of step 154 is undertaken for purposes of determining whether the first in-service part is changing normally or abnormally (step 156). If the comparison with the resonance standard (step 154) determines that the first in-service part is changing abnormally, the sort protocol 150 proceeds from step 156 to step 160. A first in-service part that is changing abnormally may be rejected by the sort protocol 150 pursuant to step 160 (e.g., the first in-service part may be designated to be taken out of service). A first in-service part that is changing normally is accepted by the sort protocol 150 pursuant to step 158 (e.g., the first in-service part may be returned to service).

The resonance standard associated with step 154 may include actual and/or projected/predicted resonance inspection results. Moreover, these resonance inspection results may be from various points in time over the life cycle of a part (e.g., resonance inspection results when in the form of a new production part, resonance inspection results at or associated with 5,000 cycles of usage, resonance inspection results at or associated with 10,000 cycles of usage, resonance inspection results at or associated with 15,000 cycles of usage, and so forth). Step 156 of the sort protocol 150 may or may not take usage data (e.g., hours or cycles of operation) into account when assessing a particular in-service part. For instance, step 156 could be configured so that resonance inspection results from the in-service part being assessed via the sort protocol 150 would have to "match" data in the resonance standard having the same or comparable usage data (e.g., if the in-service part that was being assessed via the sort protocol 150 was at 10,000 cycles of usage, step 156 could be configured such that resonance inspection results from this in-service part would have to match data in the resonance standard that are also associated with 10,000 cycles of usage). Step 156 could also be configured so that resonance inspection results from the in-service part being assessed via the sort protocol 150 would only need to "match" data in the resonance standard, regardless of any associated usage data (e.g., step 156 could be configured to determine that a part at 10,000 cycles was changing normally, even though its resonance inspection results "matched" data in the resonance standard that was in fact associated with 20,000 cycles).

The resonance standard associated with step 154 of the sort protocol 150 of FIG. 6 may be of various forms. Representative resonance standards are shown in FIG. 6. The resonance standard for step 154 may be in the form of: 1) spectra from one or more other in-service parts (e.g., spectra from a resonance inspection previously conducted on one or more in-service parts other than that being inspected pursuant to the sort protocol 150 (box 162a); 2) one or more spectra from a population of other in-service parts (box 162b); 3) resonance inspection results predicted and/or derived via mathematical modeling (box 162c); and 4) spectra obtained from accelerated life testing (box 162d).

The resonance standard associated with step 154 of the sort protocol 150 could be in the form of any one or more of the type of spectra 124 shown in FIG. 4 (e.g., box 162a). If the resonance inspection results from the resonance inspection conducted pursuant to step 152 matched or complied with any of these spectra 124 in one or more respects, the in-service part could be accepted by step 158 of the sort protocol 150.

The resonance standard used by step 154 of the sort protocol 150 may be based upon a population of in-service parts (box 162b). This population of in-service parts does not need to include the first in-service part that is being assessed by the sort protocol 150. The population of in-service parts may be viewed as a "peer group" for purposes of assessing the first in-service part via the sort protocol 150 (e.g., other parts manufactured in accordance with common specifications and/or that are functionally interchangeable with the first in-service part). For instance, the resonance standard may be in the form of spectra (e.g., spectra 124 from FIG. 4) from each of a plurality of in-service parts that are within the population. If the comparison of step 154 determines that the resonance inspection results from the first in-service part (step 152) match or comply with any of these spectra from the population in one or more respects, the first in-service part may be accepted pursuant to step 158 of the sort protocol 150. The resonance standard associated with step 154 may also be in the form of an average of spectra from each of a plurality of in-service parts that are within the noted population. If the comparison of step 154 determines that the resonance inspection results (step 152) match or comply with this spectral average from the population in one or more respects, the first in-service part may be accepted pursuant to step 158 of the sort protocol 150.

The resonance standard associated with step 154 of the sort protocol 150 may also be provided by mathematical modeling (box 162c). This mathematical modeling may be used to generate resonance inspection results for various times over the life of a part that is changing normally. If the comparison of step 154 determines that the resonance inspection results (step 152) match or comply with any of these mathematically derived resonance inspection results in one or more respects, the first in-service part may be accepted pursuant to step 158 of the sort protocol 150.

The resonance standard associated with step 154 of the sort protocol 150 may also be provided by accelerated life testing (box 162d). Resonance inspection results may be acquired as a part undergoes accelerated life testing, and these resonance inspection results may be used by the resonance standard associated with step 154. If the comparison of step 154 determines that the resonance inspection results (step 152) match or comply with any of the resonance inspection results acquired during the accelerated life testing in one or more respects, the first in-service part may be accepted pursuant to step 158 of the sort protocol 150.

Figure 7:
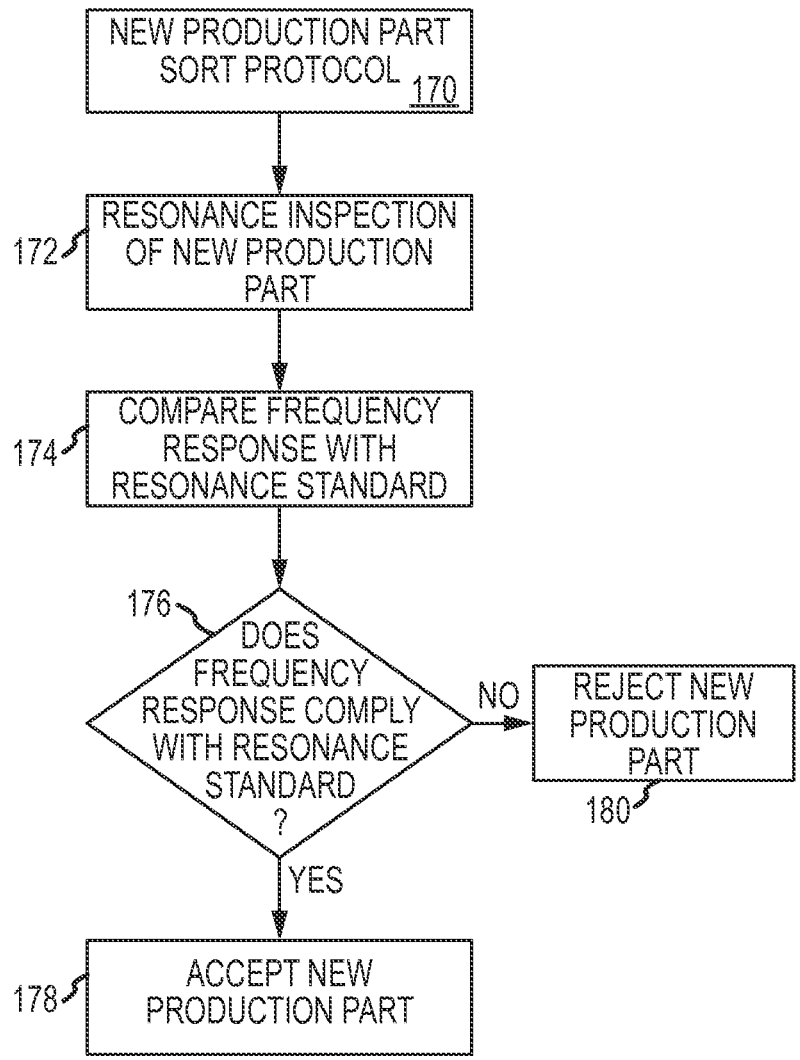
FIG. 7 is one embodiment of a sort protocol for new production parts that may be utilized for conducting a resonance inspection with the inspection tool of FIG. 3.

One embodiment of a sort protocol for new production parts is presented in FIG. 7, is identified by reference numeral 170, and may be used by the inspection tool 100 of FIG. 3. A resonance inspection of a new production part (e.g., part 120 shown in FIG. 3) is conducted pursuant to step 172 of the sort protocol 170 of FIG. 7 (e.g., via execution of the resonance inspection protocol 130 of FIG. 5). The frequency response of the new production part is compared with at least one resonance standard pursuant to step 174. Each such "resonance standard" may be incorporated by the library 118 used by the inspection tool 100 (FIG. 3) and/or may be utilized by the new production part sort logic 112, and in any case may characterize or define what should be a "normal" new production part. That is, the comparison of step 174 is undertaken for purposes of determining whether the new production part is "normal" (step 176). A new production part that does not comply with the relevant resonance standard(s) may be rejected by the sort protocol 170 pursuant to step 180 (e.g., the new production part may be designated for scrapping). A new production part that complies with the relevant resonance standard(s) is accepted by the sort protocol 170 pursuant to step 178 (e.g., the new production part may be designated for service).

The inspection tool 100 of FIG. 3 may include the above-noted surface defect assessment module 190. Generally, the surface defect assessment module 190 may be used to assess the part-under-test 120 for the existence of one or more surface defects. It is not required that the surface defect assessment module 190 be configured to identify the number and/or location of any surface defects. Instead, the surface defect assessment module 190 may simply be configured in a pass/fail mode ("pass" meaning that the surface defect assessment module 190 is accepting the part-under-test 120 based upon the lack of a surface defect trigger condition; "fail" meaning that the surface defect assessment module 190 is rejecting the part-under-test 120 based upon the existence of a surface defect trigger condition).

The surface defect assessment module 190 relies upon surface acoustical waves—a specialized type of resonance vibration that moves only at or very near the surface of the part-under-test 120. Generally speaking, surface acoustical waves penetrate the part-under-test 120 by only a single wavelength, and may be used by. The frequency of surface acoustical waves can be calculated by the following equations:

$$v_{shear} = \sqrt{(C_{66}/\rho)} \quad [1]$$

$$v_{surf} = A * v_{shear}, \text{ where } 0.9 < A < 0.95 \quad [2]$$

$$f_{SAW} = v_{surf}/\lambda, \text{ where } C/\lambda = integer \quad [3]$$

where $v_{shear}$ is the shear velocity, $C_{66}$ is an elastic modulus, $\rho$ is the density, $f_{SAW}$ is the SAW mode frequency, $v_{surf}$ is the surface velocity, $\lambda$ is the wavelength of the SAW, and C is the ball circumference. For silicon nitride, the $C_{66}$ ranged from 116 to 120 GPa, and p was approximately 3.2 g/cm³. While Equation [2] provides an estimate of the surface velocity, the actual surface velocity may be determined from empirical data.

Figure 8:
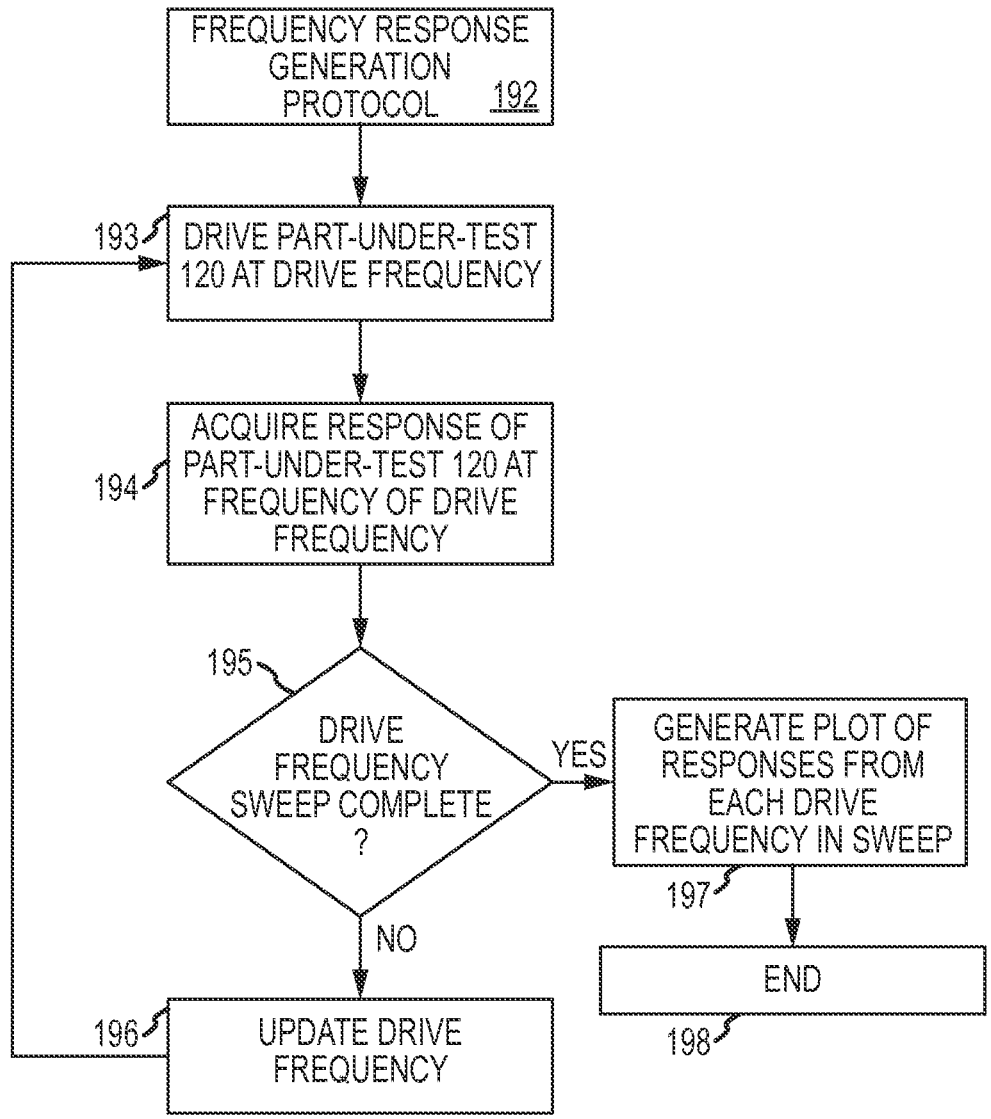
FIG. 8 is one embodiment of a protocol for generating a frequency response that may be used by the surface defect inspection module of the inspection tool of FIG. 3.

A frequency response generation protocol that may be used by the surface defect assessment module 190 (FIG. 3) is illustrated in FIG. 8 and is identified by reference numeral 192. The protocol 192 may be executed by the inspection tool 100 shown in FIG. 3. In any case, the part-under-test 120 is excited by a drive frequency (step 193; e.g., utilizing the signal generator 102 and at least one transducer 104 from the inspection tool 100 of FIG. 3). A response of the part-under-test 120 is acquired at the same frequency that is used to excite the part-under-test 120 (step 194; e.g., using one or more transducers 106 and/or the transducer 104 of the inspection tool of FIG. 3). For instance, if step 193 entails inputting a drive frequency of frequency of 3,000 kHz, step 194 is directed to acquiring the response of the part-under-test 120 at a frequency of 3,000 kHz.

The part-under-test 120 may be excited through a range of frequencies to acquire data for the surface defect assessment module 190. Any appropriate range of frequencies may be used by the protocol 192 (and may be made available to the protocol 192 in any appropriate manner; e.g., hard-coded; via user input). In this regard, step 195 of the protocol 192 is directed to determining whether the desired frequency sweep has been completed. If not, the protocol 192 proceeds to step 196 where the drive frequency is updated (e.g., the drive frequency is changed; a different drive frequency is "selected"). Control of the protocol 192 is then returned to step 193 for repetition in accordance with the foregoing.

Once the part-under-test 120 has been driven at each of the desired frequencies (step 193), the frequency response generation protocol 192 proceeds from step 195 to step 197. Step 197 of the protocol 192 is directed to generating a plot of the responses (step 194) to each drive frequency used by the protocol 192 (steps 193 and 196). Once this plot (step 197) is generated, the protocol 192 may be terminated (step 198) and the plot may then be used by the surface defect assessment module 190 to determine if the part-under-test 120 includes one or more surface defects in the manner described herein.

Figure 9A:
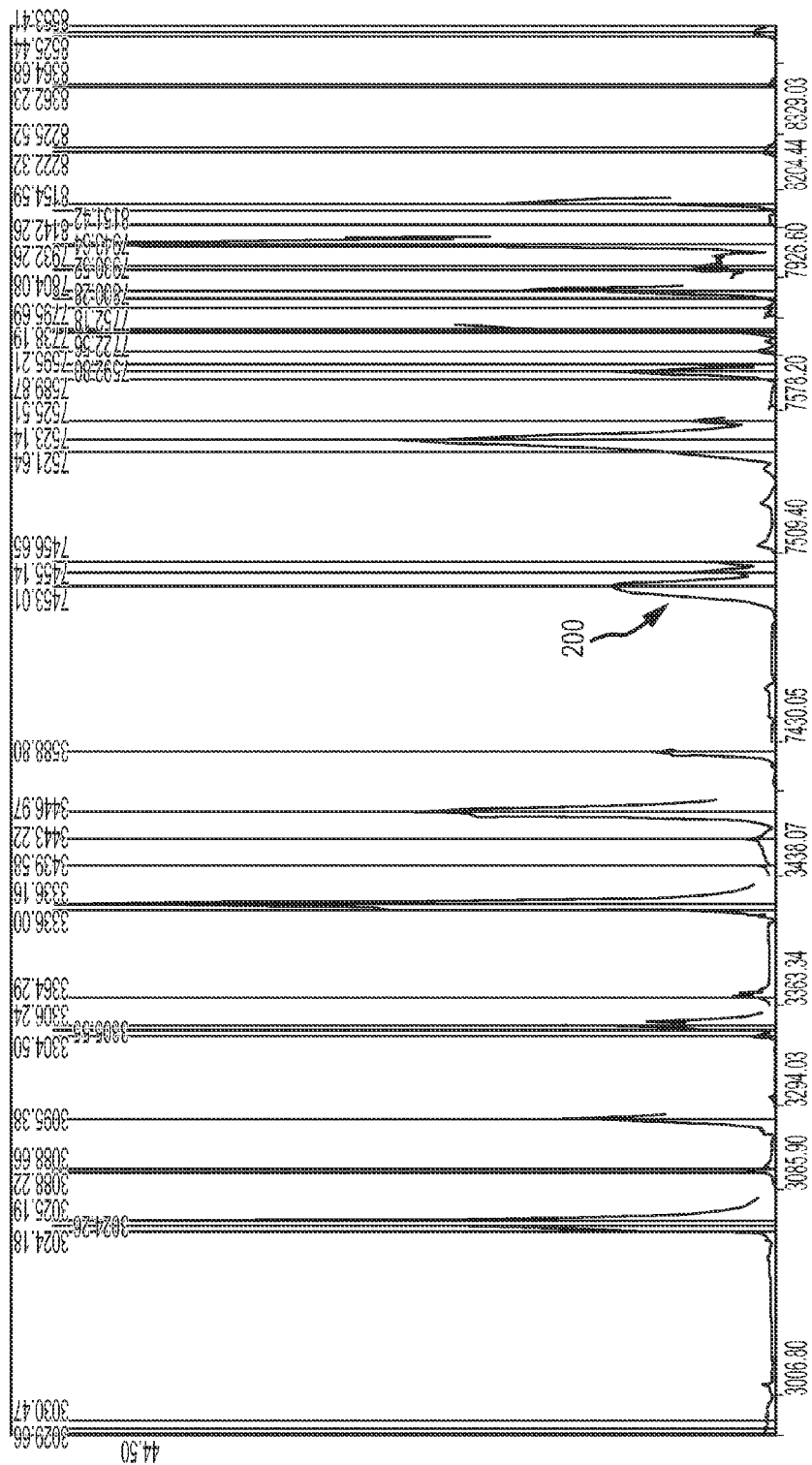
FIG. 9A is one embodiment of a frequency response that may be generated through execution of the protocol of FIG. 8.

A representative frequency response that may be generated through execution of the frequency response generation protocol 192 (FIG. 8) is presented in FIG. 9A and is identified by reference numeral 200. The frequency response 200 includes a plurality of peaks at various different frequencies. Various types of peaks may appear in the frequency response 200, including without limitation peaks that correspond with a surface acoustical wave (SAW) mode, with a resonance frequency of the part-under-test 120, or possibly with the existence of one or more surface defects on the part-under-test 120.

Figure 9B:
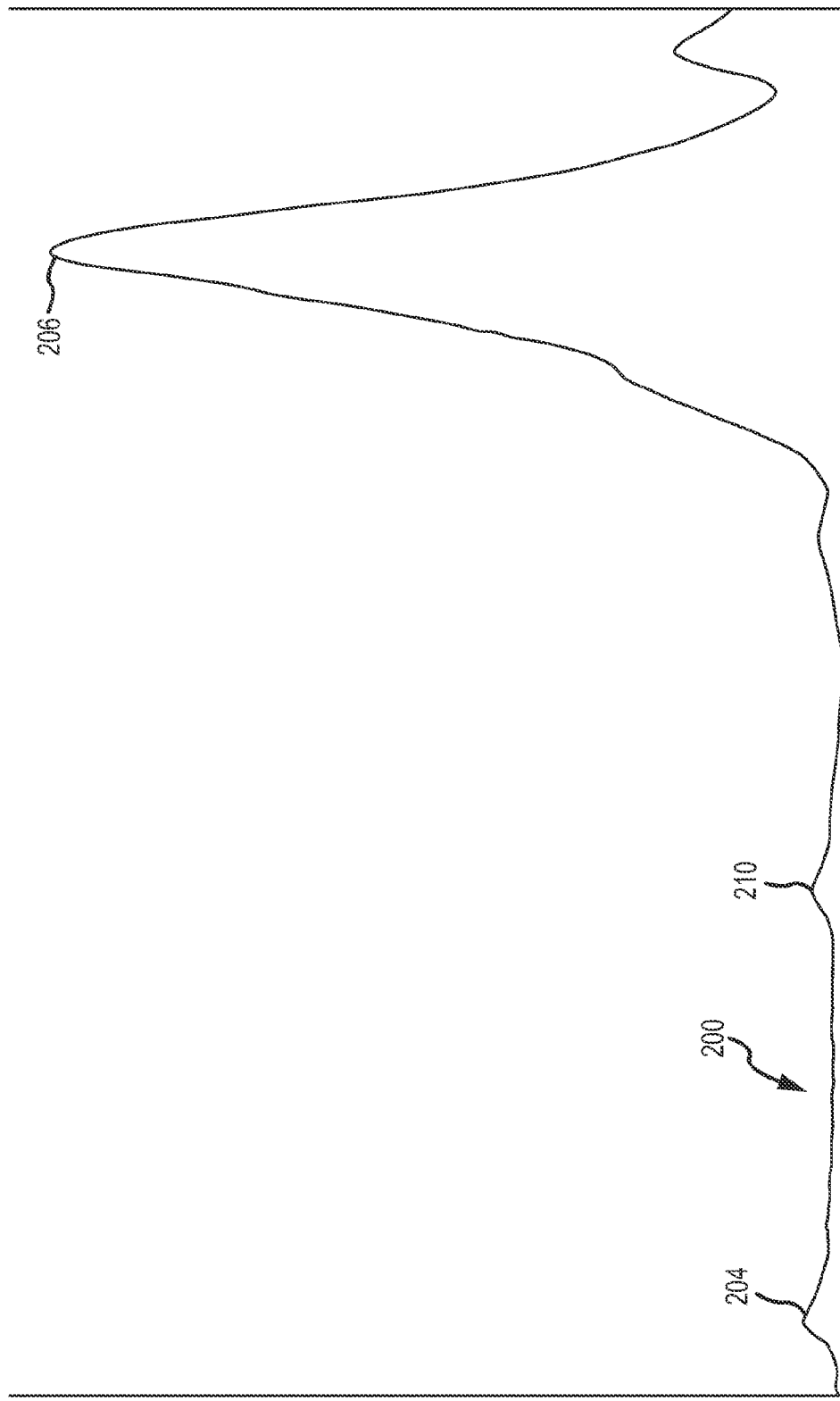
FIG. 9B illustrates an enlarged view of a representative degeneracy assessment zone that may exist in the frequency response of FIG. 9A.

FIG. 9B illustrates an enlarged portion of the frequency response 200 from FIG. 9A. Here this portion of the frequency response 200 includes a single SAW mode 206, a single reference peak 204 (e.g., a resonance peak), and a single degenerate peak 210 that may be indicative of the existence of one or more surface defects on the part-under-test 120. Multiple degenerate peaks 210 could exist between a SAW mode 206 and a reference peak 204.

The SAW modes 206 in the frequency response 200 may be identified in any appropriate manner. For instance, the frequencies at which a SAW mode 206 should exist may be mathematically determined, and the frequency response 200 may be assessed to look for peaks at or around these mathematically-determined frequencies. Peaks at or around these mathematically-determined frequencies may be characterized as SAW modes 206 for purposes of the surface defect assessment module 190. Other ways of identifying the SAW modes 206 in the frequency response 200 include mathematically determining the interval at which SAW modes 206 should appear, and then assessing the frequency response 200 to identify peaks that at least generally comply with this interval.

A reference peak 204 may be characterized as a peak that does not appreciably shift in response to the existence of one or more surface defects on the part under-test 120. Representative peaks that may be used as a reference peak 204 include without limitation resonance peaks, shear modes, whispering gallery modes, longitudinal modes, and the like. Reference peaks 204 in the frequency response 200 may be identified in any appropriate manner. The frequencies at which resonance peaks should exist may be mathematically determined, and the frequency response 200 may be assessed to look for peaks at or around these mathematically-determined frequencies. Reference peaks may also be identified in the frequency response 200 in the manner disclosed in co-pending U.S. Provisional Patent Application Ser. No. 61/498,656, the subject matter of which is incorporated by reference in its entirety herein.

One or more degenerate peaks 210 may appear in the frequency response 200 in conjunction with one or more SAW modes 206. Degenerate peaks 210 are distinguishable from noise or the like in the frequency response 200. A peak in the frequency response 200 may be characterized as a degenerate peak 210 if it satisfies at least each of the following thresholds: 1) a predetermined amplitude threshold; 2) a predetermined threshold for the magnitude of the second derivative; and 3) a zero crossing width threshold. A peak in the frequency response 210 may also be required to have a threshold SAW mode amplitude ratio (e.g., a threshold regarding the ratio of the amplitude of the peak to the amplitude of the SAW mode 206, or vice versa), a reference peak amplitude ratio (e.g., a threshold regarding the ratio of the amplitude of the peak to the amplitude of the reference peak 204, or vice versa), or both.

Figure 10A:
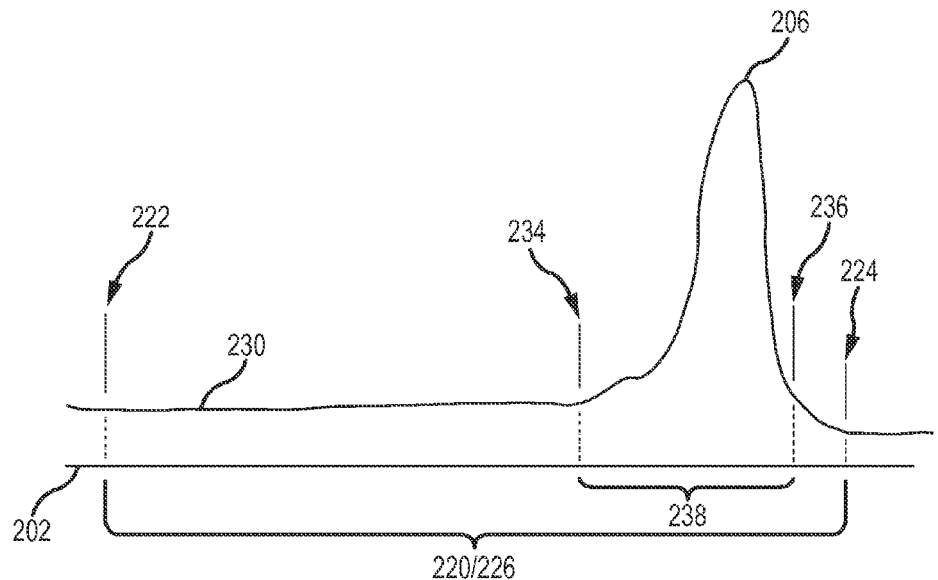
FIG. 10A illustrates a representative baseline frequency response that is annotated for use with a first embodiment of what may be referred to as an area-based surface defect assessment approach.

Part of a representative baseline frequency response that may be generated through execution of the frequency response generation protocol 192 (FIG. 8) is presented in FIG. 10A and is identified by reference numeral 230. The baseline frequency response 230 may be associated with and/or indicative of a defect-free or "acceptable" part-under-test 120. The illustrated portion of the baseline frequency response 230 includes a single SAW mode 206. Multiple SAW modes 206 would typically be included in the baseline frequency response 230 (each being defined by a different, non-overlapping range of frequencies).

Figure 12:
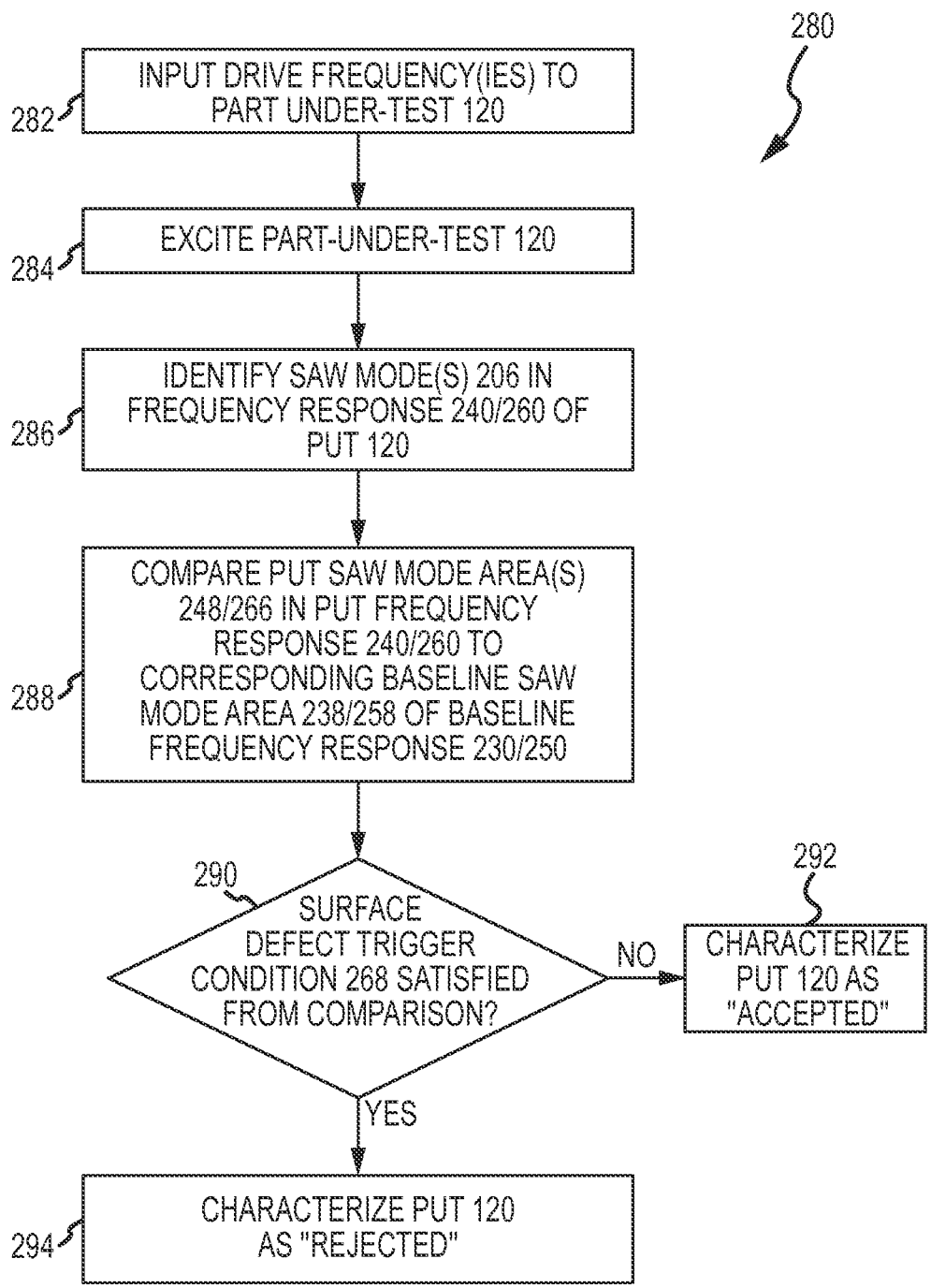
FIG. 12 is one embodiment what of may be referred to as an area-based surface defect assessment protocol that may be used by the surface defect inspection module of the inspection tool of FIG. 3.
Figure 13:
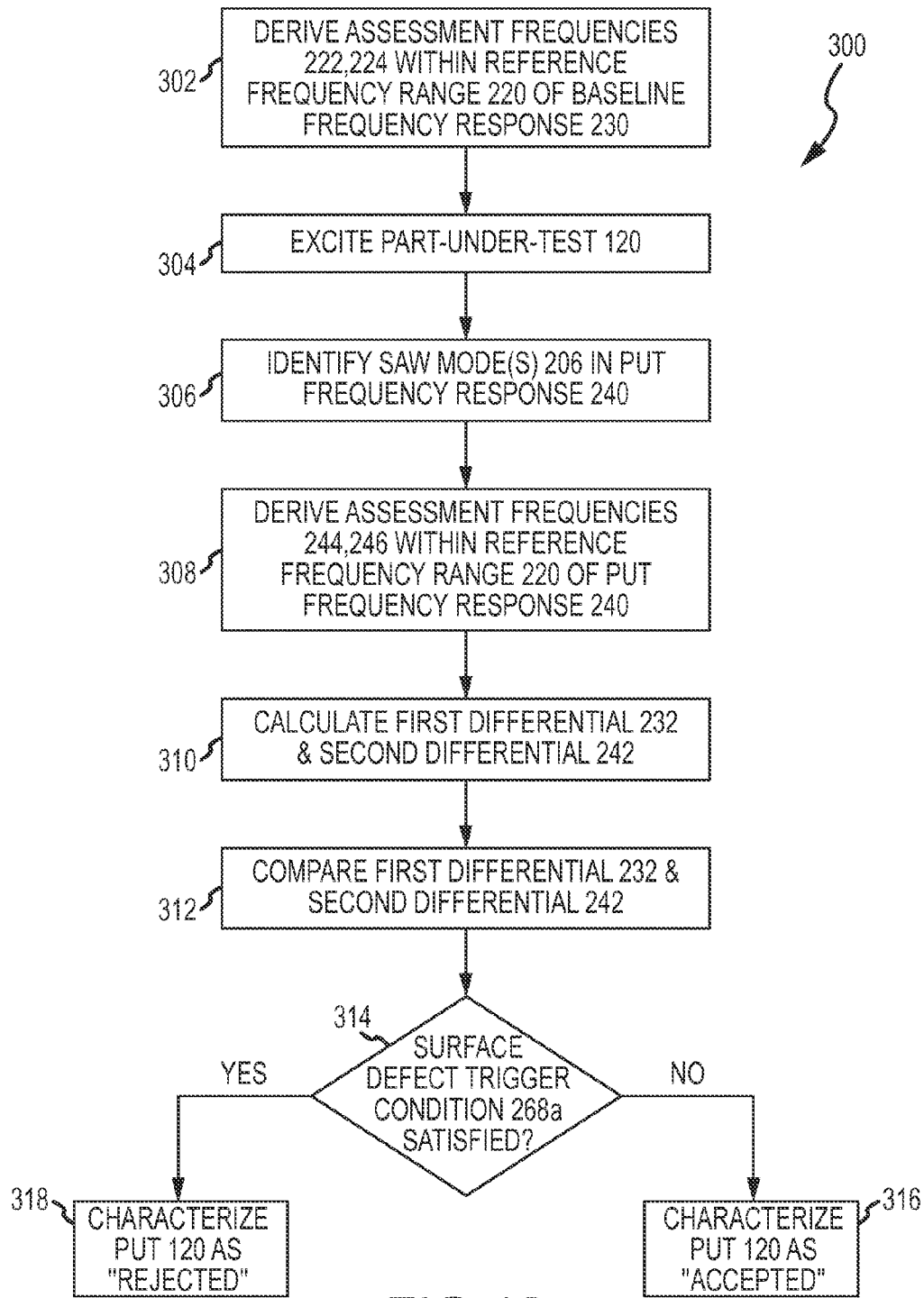
FIG. 13 is an embodiment of what may be referred to as an area-based surface defect assessment protocol that may be used by the surface defect inspection module of the inspection tool of FIG. 3, and that may be described in relation to the baseline frequency response and part-under-test frequency response presented in FIGS. 10A and 10B, respectively.

The baseline frequency response 230 of FIG. 10A is annotated for discussion in relation to the surface defect assessment protocol 280 of FIG. 12 and the surface defect assessment protocol 300 of FIG. 13. In this regard, the baseline frequency response 230 is displayed with reference to a baseline 202 (the frequency increasing from left-to-right along the baseline 202). A reference frequency range 220 extends between a first reference frequency 222 and a second reference frequency 224. The area under the baseline frequency response 230 for the reference frequency range 220 may be referred to as a reference frequency range area 226.

A first assessment frequency 234 and a second assessment frequency 236 are also displayed in relation to the baseline frequency response 230 of FIG. 10A. Each of the assessment frequencies 234, 236 are within the reference frequency range 220. Moreover, the first assessment frequency 234 and the second assessment frequency 236 encompass all or at least a substantial portion of a single SAW mode 206. The area under the baseline frequency response 230 between the assessment frequencies 234, 236 may be referred to as a baseline SAW mode area 238.

Figure 10B:
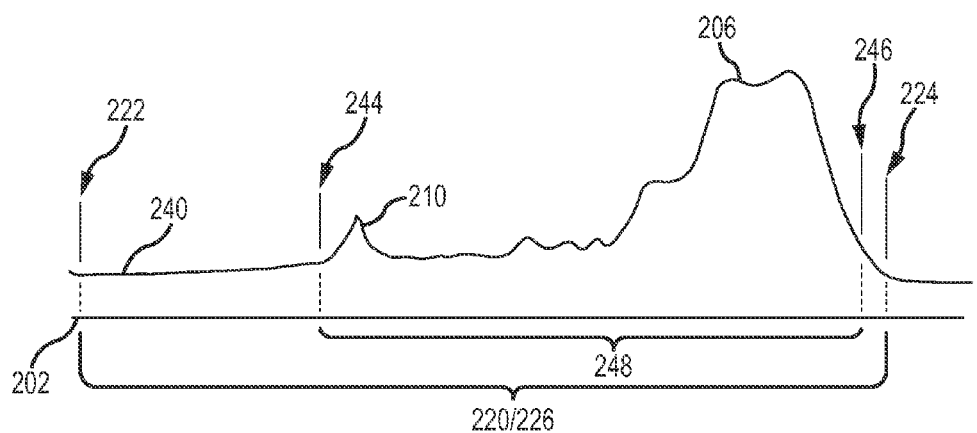
FIG. 10B illustrates a representative part-under-test frequency response that is annotated for use with the first embodiment of the area-based surface defect assessment approach.

Part of a representative part-under-test or PUT frequency response that may be generated through execution of the frequency response generation protocol 192 (FIG. 8) is presented in FIG. 10B and is identified by reference numeral 240. The PUT frequency response 240 may be associated with and/or indicative of a defective or "unacceptable" part-under-test 120. The illustrated portion of the PUT frequency response 240 includes a single SAW mode 206 (corresponding with the SAW mode 206 presented in the baseline frequency response 230 of FIG. 10A). Multiple SAW modes 206 would typically be included in the PUT frequency response 240 (each being defined by a different, non-overlapping range of frequencies). The illustrated portion of the PUT frequency response 240 also includes a single degenerate peak 210 that may be indicative of the existence of one or more surface defects on the part-under-test 120. Multiple degenerate peaks 210 could exist between a pair of adjacent SAW modes 206 in the PUT frequency response 240.

The PUT frequency response 240 of FIG. 10B is annotated for discussion in relation to the surface defect assessment protocol 280 of FIG. 12 and the surface defect assessment protocol 300 of FIG. 13. In this regard, the PUT frequency response 240 is displayed with reference to a baseline 202 (the frequency increasing from left-to-right along the baseline 202). The same reference frequency range 220 presented on the baseline frequency response 230 of FIG. 10A is also presented on the PUT frequency response 240 of FIG. 10B.

A third assessment frequency 244 and a fourth assessment frequency 246 are also displayed in relation to the PUT frequency response 240. Each of the assessment frequencies 244, 246 are within the reference frequency range 220. Moreover, the third assessment frequency 244 and the fourth assessment frequency 246 encompass all or at least a substantial portion of a single SAW mode 206, as well as the degenerate peak 210. The area under the PUT frequency response 240 between the assessment frequencies 244, 246 may be referred to as a PUT SAW mode area 248.

Figure 11A:
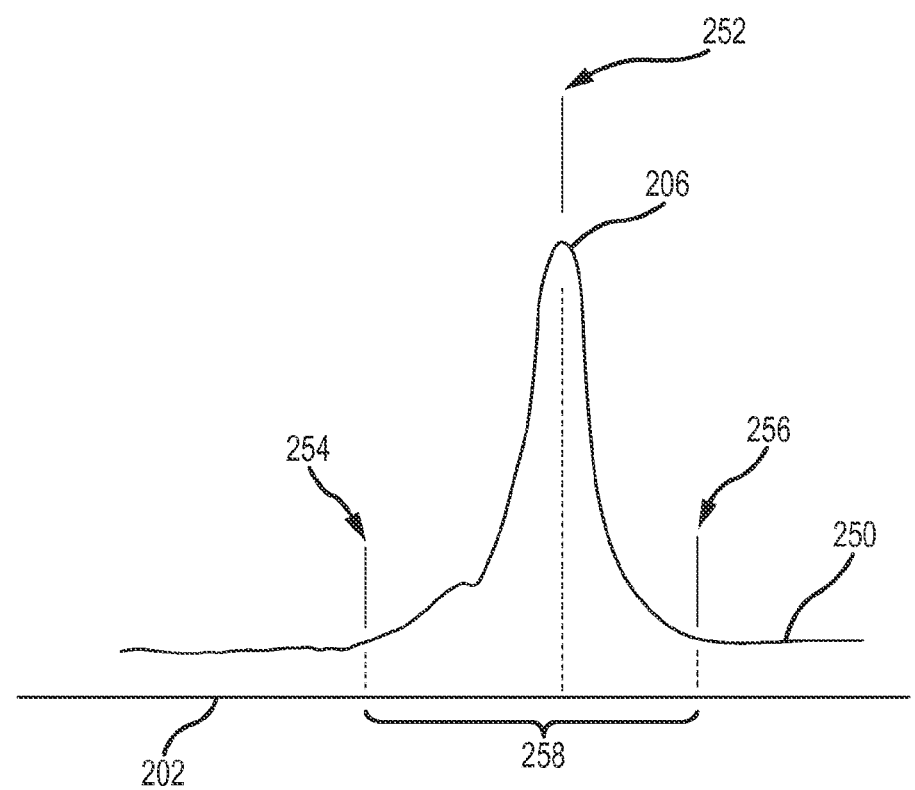
FIG. 11A illustrates a representative baseline frequency response that is annotated for use with a second embodiment of what may be referred to as an area-based surface defect assessment approach.

Part of another representative baseline frequency response that may be generated through execution of the frequency response generation protocol 192 (FIG. 8) is presented in FIG. 11A and is identified by reference numeral 250. The baseline frequency response 250 may be associated with and/or indicative of a defect-free or "acceptable" part-under-test 120. The illustrated portion of the baseline frequency response 250 includes a single SAW mode 206. Multiple SAW modes 206 would typically be included in the baseline frequency response 250 (each being defined by a different, non-overlapping range of frequencies).

Figure 14:
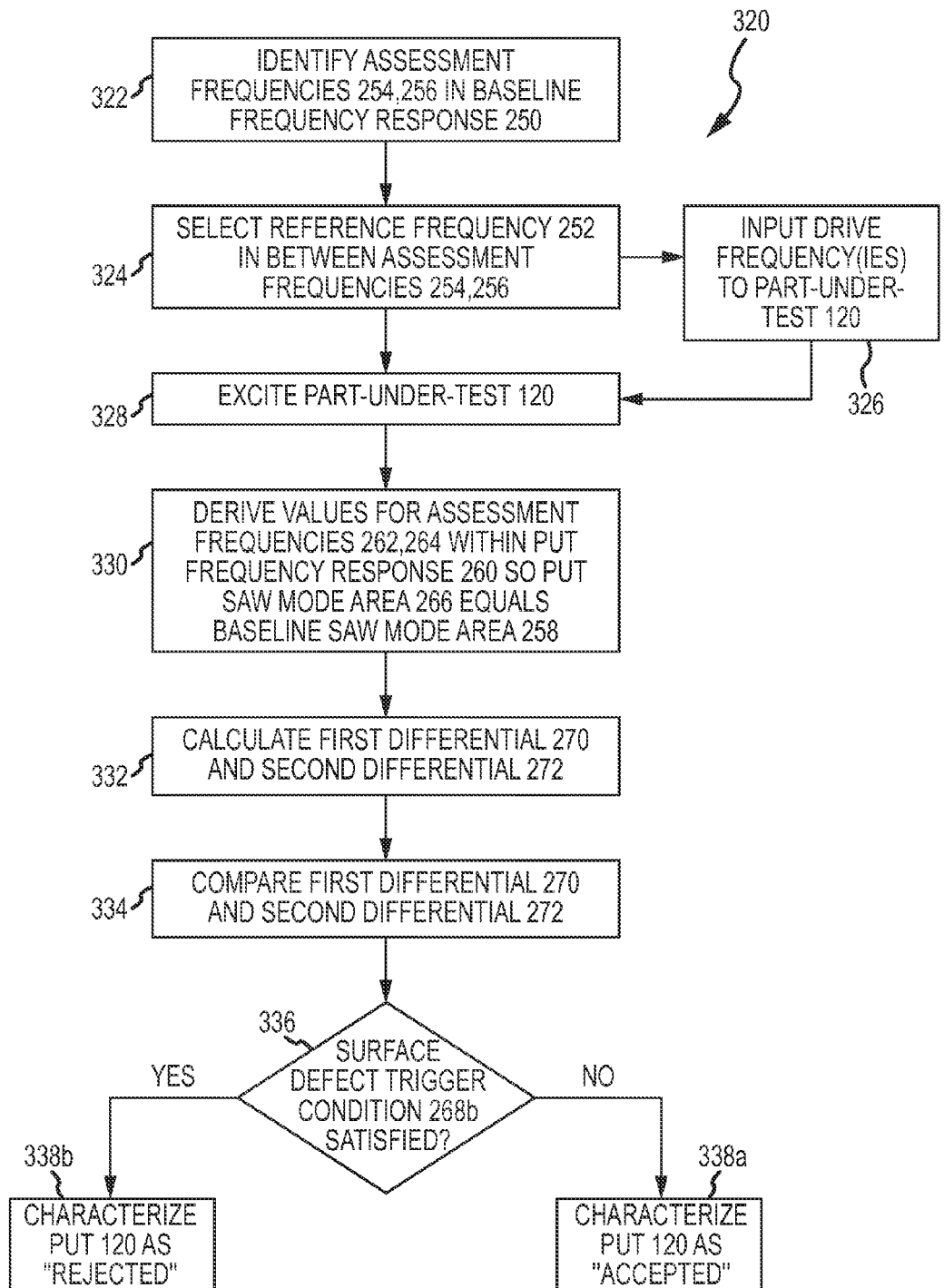
FIG. 14 is an embodiment of what may be referred to as an area-based surface defect assessment protocol that may be used by the surface defect inspection module of the inspection tool of FIG. 3, and that may be described in relation to the baseline frequency response and part-under-test frequency response presented in FIGS. 11A and 11B, respectively.

The baseline frequency response 250 of FIG. 11A is annotated for discussion in relation to the surface defect assessment protocol 280 of FIG. 12 and the surface defect assessment protocol 320 of FIG. 14. In this regard, the baseline frequency response 250 is displayed with reference to a baseline 202 (the frequency increasing from left-to-right along the baseline 202). A first assessment frequency 254 and a second assessment frequency 256 are also displayed in relation to the baseline frequency response 250. The first assessment frequency 254 and the second assessment frequency 256 encompass all or at least a substantial portion of a single SAW mode 206. The area under the baseline frequency response 250 between the assessment frequencies 254, 256 may be referred to as a baseline SAW mode area 258.

A reference frequency 252 is also displayed on the baseline frequency response 250. The reference frequency 252 is located between the first assessment frequency 254 and the second assessment frequency 256. In one embodiment, the reference frequency 252 is selected such that the area under the baseline frequency response 250 between the first assessment frequency 254 and the reference frequency 252 is equal to the area under the baseline frequency response 250 between the reference frequency 252 and the second assessment frequency 256. Other values for the reference frequency 252 (but still between the first assessment frequency 254 and the second assessment frequency 256) may be appropriate.

Figure 11B:
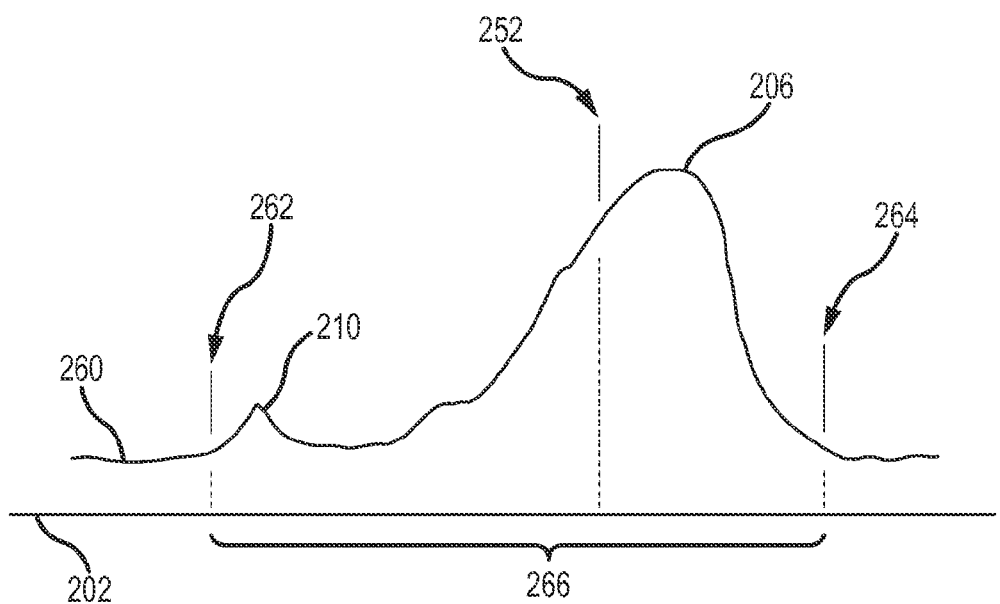
FIG. 11B illustrates a representative part-under-test frequency response that is annotated for use with the second embodiment of the area-based surface defect assessment approach.

Part of a representative part-under-test or PUT frequency response that may be generated through execution of the frequency response generation protocol 192 (FIG. 8) is presented in FIG. 11B and is identified by reference numeral 260. The PUT frequency response 260 may be associated with and/or indicative of a defective or "unacceptable" part-under-test 120. The illustrated portion of the PUT frequency response 260 includes a single SAW mode 206 (corresponding with the SAW mode 206 presented in the baseline frequency response 250). Multiple SAW modes 206 would typically be included in the PUT frequency response 260 (each being defined by a different, non-overlapping range of frequencies). The illustrated portion of the PUT frequency response 260 also includes a single degenerate peak 210 that may be indicative of the existence of one or more surface defects on the part-under-test 120. Multiple degenerate peaks 210 could exist between a pair of adjacent SAW modes 206 in the PUT frequency response 260.

The PUT frequency response 260 of FIG. 11B is annotated for discussion in relation to the surface defect assessment protocol 280 of FIG. 12 and the surface defect assessment protocol 320 of FIG. 14. In this regard, the PUT frequency response 260 is displayed with reference to a baseline 202 (the frequency increasing from left-to-right along the baseline 202). A third assessment frequency 262 and a fourth assessment frequency 264 are also displayed in relation to the PUT frequency response 260. The third assessment frequency 262 and the fourth assessment frequency 264 encompass all or at least a substantial portion of a single SAW mode 206, as well as the degenerate peak 210. The area under the PUT frequency response 260 between the assessment frequencies 262, 264 may be referred to as a PUT SAW mode area 266. The same reference frequency 252 presented on the baseline frequency response 250 of FIG. 11A is also presented on the PUT frequency response 260 of FIG. 11B.

FIG. 12 illustrates one embodiment of a surface defect assessment protocol 280 that may be utilized by the surface defect assessment module 190 of FIG. 3, and in accordance with the foregoing. One or more drive frequencies are input to the part-under-test 120 (step 282) and excite the part-under-test 120 (step 284). A SAW mode 206 is identified in the frequency response (e.g., PUT frequency response 240 of FIG. 10B; PUT frequency response 260 of FIG. 11B) of the part-under-test 120 (step 286). The PUT SAW mode area 248/266 is compared to the corresponding baseline SAW mode area 238/258 of the baseline frequency response 230/250 (step 288) to see if a surface defect condition exists. If a surface defect trigger condition 268 (step 290) is not satisfied from the comparison of step 288, the protocol 280 proceeds from step 290 (surface defect trigger condition 268 assessment) to step 292 where the part-under-test 120 may be characterized as "non-defective" or "accepted." If the surface defect trigger condition 268 (step 290) is satisfied from the comparison of step 288, the protocol 280 proceeds from step 290 (surface defect trigger condition 268 assessment) to step 294 where the part-under-test 120 may be characterized as "defective" or "rejected."

The surface defect trigger condition 268 (step 290) may be satisfied by a surface defect condition being identified in relation to a single SAW mode 206 (step 288). The surface defect trigger condition 268 (step 290) may require that a surface defect condition be identified in relation to multiple SAW modes 206 (e.g., step 286 may be used to identify multiple SAW modes 206, step 288 may be repeated for each of these SAW modes 206, and the surface defect trigger condition 268 (step 290) may be satisfied only if a surface defect condition is identified by step 288 for each of multiple SAW modes 206).

One embodiment for the surface defect assessment protocol 280 of FIG. 12 is presented in FIG. 13 and is identified by reference numeral 300. In the case of the surface defect assessment protocol 300, one or more drive frequencies are input to the part-under-test 120 (step 302) and excite the part-under-test 120 (step 304). This may generate the PUT frequency response 240 of FIG. 10B. A SAW mode 206 is identified in the PUT frequency response 240 (step 306). The third assessment frequency 244 and the fourth assessment frequency 246 are derived pursuant to step 308 of the protocol 300.

One option for deriving the assessment frequencies 244, 246 for step 308 of the surface defect assessment protocol 300 uses the assessment frequencies 234, 236 from the corresponding baseline frequency response 230. The baseline frequency response 230 again includes a reference frequency range 220 that encompasses a single SAW mode 206. The first assessment frequency 234 and the second assessment frequency 236 may be selected so that: 1) each of the assessment frequencies 234, 236 are within the reference frequency range 220; 2) the assessment frequencies 234, 236 include all or at least a substantial portion of the same SAW mode 206; and 3) the assessment frequencies 234, 236 define a baseline SAW mode area 238 that is a predetermined percentage of the reference frequency range area 226 (the area under the baseline frequency response 230 between the first reference frequency 222 and the second reference frequency 224). The assessment frequencies 234, 236 may be at least generally adjacent to a "zero slope" region of the baseline frequency response 230.

One embodiment has the first assessment frequency 234 and second assessment frequency 236 being selected such that the baseline SAW mode area 238 is a majority of the reference frequency range area 226 (i.e., the area of the baseline frequency response 230 over the reference frequency range 220). Another embodiment has the first assessment frequency 234 and second assessment frequency 236 being selected such that the baseline SAW mode area 238 is 95% of the reference frequency range area 226 (i.e., the area of the baseline frequency response 230 over the reference frequency range 220). Another embodiment has the first assessment frequency 234 and second assessment frequency 236 being selected such that the baseline SAW mode area 238 is 99% of the reference frequency range area 226 (i.e., the area of the baseline frequency response 230 over the reference frequency range 220).

The third reference frequency 244 and the fourth assessment frequency 246 may be derived for purposes of step 308 of the surface defect assessment protocol 300 so that: 1) each assessment frequency 244, 246 is within the same reference frequency range 220 associated with the assessment frequencies 234, 236 of the baseline frequency response 230 of FIG. 10A; 2) the assessment frequencies 244, 246 include all or a substantial portion of the corresponding SAW mode 206 (in relation to the SAW mode 206 associated with the assessment frequencies 234, 236 in the baseline frequency response 230 of FIG. 10A); and 3) the assessment frequencies 244, 246 define a PUT SAW mode area 248 that is the same predetermined percentage of the reference frequency range area 226 as is the baseline SAW mode area 238 in relation to the reference frequency range area 226 (e.g., the PUT SAW mode area 248 may be of the same magnitude as the baseline SAW mode area 238).

Based upon the existence of one or more surface defects in the part-under-test 120, the SAW mode 206 in the PUT frequency response 240 (FIG. 10B) is "compressed" compared to the corresponding SAW mode 206 in the baseline frequency response 230 (FIG. 10A). This "compression" positions the third assessment frequency 244 (PUT frequency response 240) at a lower frequency than the first assessment frequency 234 (baseline frequency response 230). Although this "compression" may change the frequency of the fourth assessment frequency 246 (PUT frequency response 240) compared to the second assessment frequency 236 (baseline frequency response 230), the compression appears to primarily affect the PUT frequency response 240 at frequencies less than the frequencies that define the SAW mode 206.

Step 310 of the surface defect assessment protocol 300 of FIG. 13 is directed to calculating a first differential 232 and a second differential 242. The first differential 232 is the mathematical difference between the second assessment frequency 236 and the first assessment frequency 234 for the baseline frequency response 230 of FIG. 10A. This may be used to define a first threshold. The second differential 242 is the mathematical difference between the third assessment frequency 244 and the fourth assessment frequency 246 for the PUT frequency response 240 of FIG. 10B.

The first differential 232 (or a first threshold that is based upon the first differential 232) may be compared with the second differential 242 to determine if a surface defect condition exists (step 312). If a surface defect trigger condition 268a is not satisfied from the comparison of step 312, the protocol 300 proceeds from step 314 (surface defect trigger condition 268a assessment) to step 316 where the part-under-test 120 may be characterized as "non-defective" or "accepted." If the surface defect trigger condition 268a is satisfied from the comparison of step 312, the protocol 300 proceeds from step 314 (surface defect trigger condition 268a assessment) to step 318 where the part-under-test 120 may be characterized as "defective" or "rejected."

The surface defect trigger condition 268a (step 314) may be satisfied by a surface defect condition being identified in relation to a single SAW mode 206 (step 312). The surface defect trigger condition 268a (step 314) may require that a surface defect condition be identified in relation to multiple SAW modes 206 (e.g., step 306 may identify multiple SAW modes 206, steps 308, 310, and 312 may be repeated for each of these SAW modes 206, and the surface defect trigger condition 268a may be satisfied only if a defect condition is identified by step 312 for a predetermined number of different SAW modes 206).

A surface defect condition (the comparison of step 312) may be equated with the second differential 242 being at least a predetermined amount larger than the first differential 232 (and which may define a first threshold). As such, step 302 and the calculation of the first differential 232 (step 310) may not be executed on each execution of the surface defect assessment protocol 300 (this may be done once and "stored" as the noted "first threshold"). Moreover, step 312 may in fact be configured to determine if the second differential 242 satisfies this first threshold (e.g., to determine if the second differential 242 is at least a predetermined amount larger than the first differential 232—if it is, the second differential 242 may be characterized as "satisfying" the first threshold).

A surface defect condition for purposes of step 312 may be equated as existing when there is a predetermined relationship between the noted second differential 242 and the noted first differential 232. In one embodiment, a surface defect condition is equated with the second differential 242 being at least 15% larger than the first differential 232. In one embodiment, a surface defect condition is equated with the second differential 242 being at least 30% larger than the first differential 232. In one embodiment, a surface defect condition is equated with the first differential 232 being no more than 70% of the second differential 242. In one embodiment, a surface defect condition is equated with the first differential 232 being no more than 85% of the second differential 242 in another embodiment.

Another embodiment for the surface defect assessment protocol 280 of FIG. 12 is presented in FIG. 14 and is identified by reference numeral 320. In the case of the surface defect assessment protocol 320, the first assessment frequency 254 and the second assessment frequency 256 are identified in the baseline frequency response 250 of FIG. 11A. The first assessment frequency 254 and the second assessment frequency 256 may be selected so that the assessment frequencies 254, 256 include all or at least a substantial portion of a given SAW mode 206. In one embodiment, the assessment frequencies 254, 256 may be at least generally adjacent to a "zero slope" region of the baseline frequency response 250. A reference frequency 252 is selected pursuant to step 324 of the surface defect assessment protocol 320.

Again and as discussed above, this reference frequency 252 is located between the first assessment frequency 254 and the second assessment frequency 256. In one embodiment, the reference frequency 252 is selected such that the area under the baseline frequency response 250 between the first assessment frequency 254 and the reference frequency 252 is equal to the area under the baseline frequency response 250 between the reference frequency 252 and the second assessment frequency 256. Other values for the reference frequency 252 (but still between the first assessment frequency 254 and the second assessment frequency 256) may be appropriate.

One or more drive frequencies are input to the part-under-test 120 (step 326) and excite the part-under-test 120 (step 328). This may generate the PUT frequency response 260. Steps 322 and 324 will typically be executed prior to the execution of steps 326 and 328 (and in fact may not be executed on each execution of the protocol 320). However, steps 322 and 324 only need be executed before step 330 of the protocol 320.

Step 330 of the surface defect assessment protocol 320 of FIG. 14 is directed to deriving values for the third assessment frequency 262 and the fourth assessment frequency 264 of the PUT frequency response 260. The third reference frequency 262 and the fourth assessment frequency 264 may be derived for purposes of step 330 of the surface defect assessment protocol 320 so that: 1) the assessment frequencies 262, 264 include all or at least a substantial portion of the corresponding SAW mode 206 (in relation to the SAW mode 206 associated with the assessment frequencies 254, 256 in the baseline frequency response 250 of FIG. 11A); and 2) the assessment frequencies 262, 264 define a PUT SAW mode area 266 that is of the same magnitude as the baseline SAW mode area 258 (associated with the assessment frequencies 254, 256 of the baseline frequency response 250 of FIG. 11A).

Based upon the existence of one or more surface defects in the part-under-test 120, the SAW mode 206 in the PUT frequency response 260 (FIG. 11B) is "compressed" compared to the corresponding SAW mode 206 in the baseline frequency response 250 (FIG. 11A). This "compression" positions the third assessment frequency 262 (PUT frequency response 260) at a lower frequency than the first assessment frequency 254 (baseline frequency response 250). Although this "compression" may change the frequency of the fourth assessment frequency 264 (PUT frequency response 260) compared to the second assessment frequency 256 (baseline frequency response 250), the compression appears to primarily affect the PUT frequency response 260 at frequencies less than the frequencies that define the SAW mode 206.

Step 332 of the surface defect assessment protocol 320 of FIG. 14 is directed to calculating a first differential 270 and a second differential 272. The first differential 272 is the mathematical difference between the reference frequency 252 and the third assessment frequency 262 for the PUT frequency response 260 of FIG. 11B. The second differential 272 is the mathematical difference between the fourth assessment frequency 264 for the PUT frequency response 260 of FIG. 11B and the reference frequency 252.

The first differential 270 is compared with the second differential 272 to determine if a surface defect condition exists (step 334). If a surface defect trigger condition 268*b* is not satisfied from the comparison of step 334, the protocol 320 proceeds from step 336 (surface defect trigger condition 268*b* assessment) to step 338*a* where the part-under-test 120 may be characterized as "non-defective" or "accepted." If the surface defect trigger condition 268*b* is satisfied from the comparison of step 334, the protocol 320 proceeds from step 336 (surface defect trigger condition 268*b* assessment) to step 338*b* where the part-under-test 120 may be characterized as "defective" or "rejected."

The surface defect trigger condition 268*b* (step 336) may be satisfied by a surface defect condition being identified in relation to a single SAW mode 206. The surface defect trigger condition 268*b* (step 336) may require that a surface defect condition be identified in relation to multiple SAW modes 206 (e.g., steps 322, 324, 330, 332, and 334 may be repeated for each of multiple SAW modes 206, and the surface defect trigger condition 268*b* may be satisfied only if a surface defect condition is identified by step 334 for multiple SAW modes 206).

A surface defect condition for purposes of step 334 may be equated as existing when there is a predetermined relationship between the noted second differential 272 and the noted first differential 270. A surface defect condition for purposes of step 334 may be equated with the first differential 270 being larger than the second differential 272 by a predetermined amount (e.g., satisfying a threshold). In one embodiment, a surface defect condition is equated with the first differential 270 being at least 100% larger than the second differential 272. A surface defect condition may be equated with the first differential 270 being at least 150% larger than the second differential 272 in one embodiment, may be equated with the first differential 270 being at least 50% larger than the second differential 272 in another embodiment, and may be equated with the first differential 270 being at least 25% larger than the second differential 272 in yet another embodiment. In one embodiment, a surface defect condition is equated with the second differential 272 being no more than 50% of the first differential 270 in one embodiment, and with the second differential 272 being no more than 40% of the first differential 270 in another embodiment.

Figure 15A:
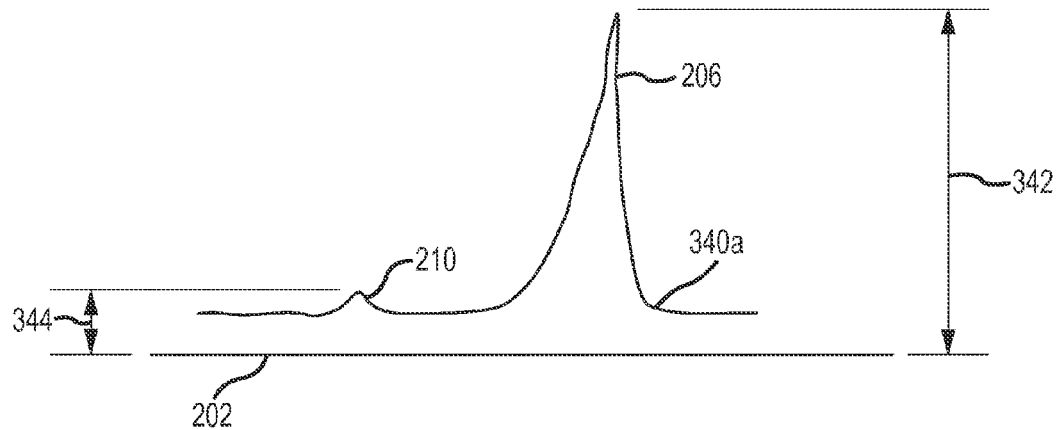
FIG. 15A illustrates a representative part-under-test frequency response with a defect of a first magnitude, and that is annotated for use with an amplitude-based surface defect assessment approach.
Figure 15B:
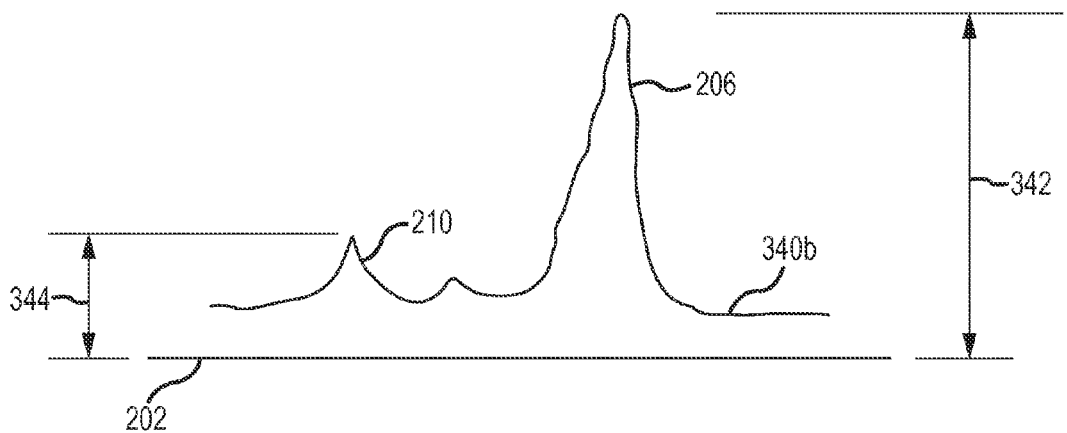
FIG. 15B illustrates a representative part-under-test frequency response with a defect of a second magnitude, and that is annotated for use with an amplitude-based surface defect assessment approach.

Part of a representative part-under-test or PUT frequency response that may be generated through execution of the frequency response generation protocol 192 (FIG. 8) is presented in each of FIGS. 15A and 15B, and are identified by reference numerals 340*a* and 340*b*, respectively. The PUT frequency response 340*a* may be associated with and/or indicative of a defective or "unacceptable" part-under-test 120 (e.g., having a surface defect of a first magnitude). The PUT frequency response 340*b* may be associated with and/or indicative of a defective or "unacceptable" part-under-test 120 (e.g., having a surface defect of a second, larger magnitude compared to the FIG. 15A).

The illustrated portion of the PUT frequency responses 340*a*, 340*b* each include a single SAW mode 206. Multiple SAW modes 206 would typically be included in the PUT frequency responses 340*a*, 340*b* (each being defined by a different, non-overlapping range of frequencies). The illustrated portion of each PUT frequency response 340*a*, 340*b* also includes a single degenerate peak 210 that may be indicative of the existence of one or more surface defects on the part-under-test 120. Multiple degenerate peaks 210 could exist between a pair of adjacent SAW modes 206 in each of the PUT frequency responses 340*a*, 340*b*.

Figure 16:
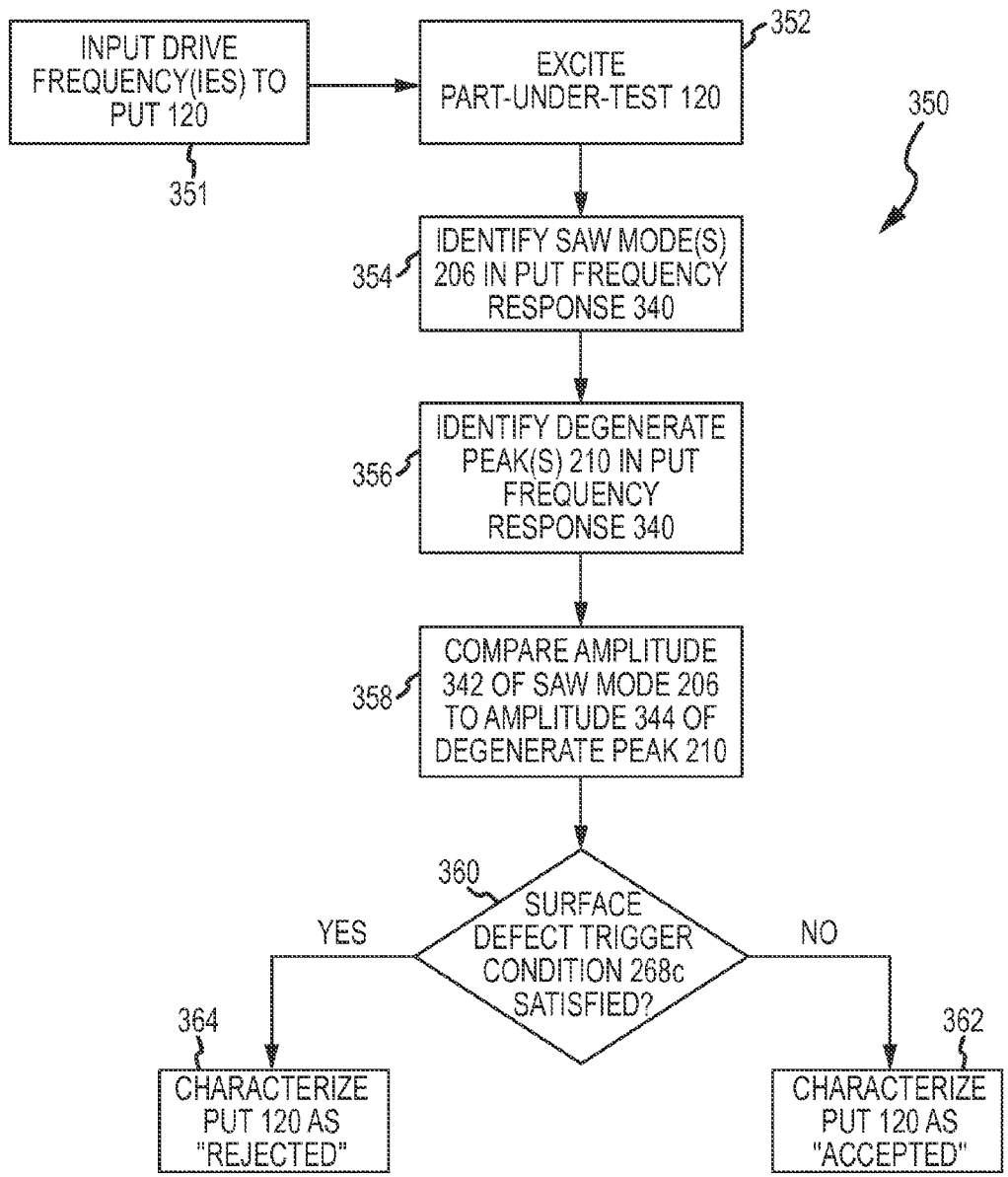
FIG. 16 is an embodiment of an amplitude-based surface defect assessment protocol that may be used by the surface defect inspection module of the inspection tool of FIG. 3, and that may be described in relation to the part-under-test frequency responses presented in FIGS. 15A and 15B.

The PUT frequency responses 340*a*, 340*b* of FIGS. 15A and 15B are each annotated for discussion in relation to the surface defect assessment protocol 350 of FIG. 16. In this regard, each PUT frequency response 340*a*, 340*b* is displayed with reference to a baseline 202 (the frequency increasing from left-to-right along the baseline 202), a first amplitude 342 is illustrated for the SAW mode 206 (measured relative to the baseline 202), and a second amplitude 344 is illustrated for the degenerate peak 210 (again, measured relative to the baseline 202).

An embodiment of an amplitude-based surface defect assessment protocol is presented in FIG. 16 and is identified by reference numeral 350. One or more drive frequencies are input to the part-under-test 120 (step 351) and excite the part-under-test 120 (step 352). This may generate the PUT frequency response 340*a* of FIG. 15A and/or the PUT frequency response 340*b* of FIG. 15B. The protocol 350 will hereafter be described in relation to a "PUT frequency response 340."

One or more SAW modes 206 may be identified in the PUT frequency response 340 (step 354). One or more degenerate peaks 210 may be identified in the frequency response 340 (step 356). The amplitude 342 of a SAW mode 206 is compared with the amplitude 344 of a degenerate peak 210 (step 358). This degenerate peak 210 may be a degenerate peak that is located between the SAW mode 206 to which it is being compared for purposes of step 358, and an adjacent SAW mode 206 defined by a set of lower frequencies. In any case, if a surface defect trigger condition 268*c* is not satisfied from the comparison of step 358, the protocol 350 proceeds from step 360 (surface defect trigger condition 268*c* assessment) to step 362 where the part-under-test 120 may be characterized as "non-defective" or "accepted." If the surface defect trigger condition 268*c* is satisfied from the comparison of step 358, the protocol 350 proceeds from step 360 (surface defect trigger condition 268*c* assessment) to step 364 where the part-under-test 120 may be characterized as "defective" or "rejected."

The surface defect trigger condition 268*c* (step 360) may be satisfied by a surface defect condition being identified in relation to a single SAW mode 206 and a single degenerate peak 210. The surface defect trigger condition 268*c* (step 360) may be satisfied by a surface defect condition being identified in relation to a single SAW mode 206 and a predetermined number of degenerate peaks 210 (e.g., degenerate peaks 210 located between this particular SAW mode 206 and an adjacent SAW mode 206 defined by a set of lower frequencies). The surface defect trigger condition 268*c* (step 360) may require that a surface defect condition be identified in relation to multiple SAW modes 206 and one or more degenerate peaks 210 (e.g., steps 354, 356, and 358 may be repeated for each of multiple SAW modes 206, and the surface defect trigger condition 268*c* may be satisfied only if a defect condition is identified by step 358 for a predetermined number of different SAW modes 206).

A surface defect condition for purposes of step 358 may entail comparing a first threshold to the ratio of the first SAW mode amplitude 342 to the degenerate peak amplitude 344. A surface defect condition for purposes of step 358 may exist if this ratio satisfies a first threshold. A surface defect condition for purposes of step 358 may exist if this ratio is no more and/or is less than a predetermined value (e.g., the first threshold). A surface defect condition for purposes of step 358 may be equated as existing when there is a predetermined relationship between the first SAW mode amplitude 342 to the degenerate peak amplitude 344. A surface defect condition for purposes of step 358 may be equated as existing when the first SAW mode amplitude 342, divided by the degenerate peak amplitude 344, is no more than about 8 in one embodiment, and is no more than about 4 in another embodiment. A surface defect condition for purposes of step 360 may be equated as existing when the degenerate peak amplitude 344, divided by the first SAW mode amplitude 342, is at least about 12% in one embodiment, and is at least about 25% in another embodiment.

FIG. 15A illustrates a PUT 120 having a defect, while FIG. 15B illustrates a PUT 120 having a larger defect. That is, the SAW mode amplitude 342/degenerate peak amplitude 344 ratio for FIG. 15A is much larger than the SAW mode amplitude 342/degenerate peak amplitude 344 ratio for FIG. 15B. The protocol 350 could be configured to compare the SAW mode amplitude 342/degenerate peak amplitude 344 ratio from step 358 to multiple defect grades (e.g., a first defect grade having a first range of values; a second defect grade having a second, non-overlapping, range of values of smaller magnitudes). Step 364 could then be configured to identify the "magnitude" of a defect associated with the part-under-test 120 and assign the PUT 120 to a particular defect grade.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A method for identifying a surface defect on a part, comprising the steps of:
   exciting a part-under-test using at least one input frequency;
   acquiring a frequency response of said part-under-test to said exciting step and that defines a part-under-test frequency response;
   identifying a first surface acoustical wave (SAW) mode in said part-under-test frequency response;
   comparing a first SAW mode area in said part-under-test frequency response to a baseline SAW mode area of a baseline frequency response, wherein said comparing step comprises:

identifying first and second assessment frequencies for said baseline SAW mode area within said baseline frequency response;

identifying third and fourth assessment frequencies for said first SAW mode area within said part-under-test frequency response, wherein said first and second assessment frequencies for said baseline SAW mode area and said third and fourth assessment frequencies for said first SAW mode area are each within a common reference frequency range, wherein said identifying step for said first and second assessment frequencies for said baseline SAW mode area comprises deriving values for said first and second assessment frequencies such that said baseline SAW mode area is a predetermined percentage of an area of said baseline frequency response over said reference frequency range, and wherein said identifying step for said third and fourth assessment frequencies for said first SAW mode area comprises deriving values for said third and fourth assessment frequencies such that said first SAW mode area is the same said predetermined percentage of said area of said part-under-test frequency response over said reference frequency range; and comparing a relationship of said first and second assessment frequencies within said baseline frequency response to a relationship of said third and fourth assessment frequencies within said part-under-test frequency response;

assessing said part-under-test for a defect using said comparing step; and characterizing said part-under-test as being defective based upon satisfaction of a surface defect trigger condition, wherein at least part of said surface defect trigger condition is satisfied when said relationship between said third and fourth assessment frequencies for said first SAW mode area satisfies a first threshold based upon said relationship between said first and second assessment frequencies for said baseline SAW mode area.

2. The method of claim 1, wherein said part-under-test is of a symmetrical configuration.

3. The method of claim 1, wherein said part-under-test is of a configuration that is selected from the group consisting of a ball, sphere, cylinder, tapered roller, and right circular cylinder.

4. The method of claim 1, wherein at least part of said surface defect trigger condition is satisfied when a first differential of said fourth and third assessment frequencies for said first SAW mode area satisfies said first threshold, which is based upon a second differential of said second and first assessment frequencies for said baseline SAW mode area.

5. The method of claim 1, wherein said predetermined percentage is 95%.

6. The method of claim 1, wherein said predetermined percentage is 99%.

7. The method of claim 1, wherein a first differential is an absolute value of a difference between said first and second assessment frequencies, wherein a second differential is an absolute value of a difference between said third and fourth assessment frequencies, and wherein satisfaction of said first threshold comprises said second differential being at least a predetermined amount larger than said first differential.

8. The method of claim 7, wherein satisfaction of said first threshold comprises said second differential being at least 15% larger than said first differential.

9. The method of claim 7, wherein satisfaction of said first threshold comprises said second differential being at least 30% larger than said first differential.

10. A method for identifying a surface defect on a part, comprising the steps of:

deriving first and second assessment frequencies that are within a reference frequency range of a baseline frequency response and that encompass a first surface acoustical wave (SAW) mode;

exciting a part-under-test using at least one input frequency;

acquiring a frequency response of said part-under-test to said exciting step and that defines a part-under-test frequency response;

identifying a corresponding first SAW mode in said part-under-test frequency response;

deriving third and fourth assessment frequencies that are each within the same said reference frequency range of said part-under-test frequency response, wherein said reference frequency range encompasses said corresponding first SAW mode;

determining a first differential between said second and first assessment frequencies of said baseline frequency response;

determining a second differential between said fourth and third assessment frequencies of said part-under-test frequency response;

comparing said second differential with a first threshold that is based upon said first differential; and characterizing said part-under-test as being defective based upon satisfaction of a surface defect trigger condition, wherein at least part of said surface defect trigger condition is satisfied when said second differential satisfies said first threshold, and wherein said first threshold requires said second differential to be larger than said first differential by at least a predetermined amount.

11. The method of claim 10, wherein:

said deriving first and second assessment frequencies step comprises realizing an area of said baseline frequency response between said first and second assessment frequencies that is a predetermined percentage of an area of said baseline frequency response over said reference frequency range; and said deriving third and fourth further assessment frequencies step comprises realizing an area of said part-under-test frequency response between said third and fourth assessment frequencies that is said predetermined percentage of said area of said part-under-test frequency response over said reference frequency range.

12. The method of claim 11, wherein said predetermined percentage is 95%.

13. The method of claim 11, wherein said predetermined percentage is 99%.

14. The method of claim 10, wherein said first differential is an absolute value of a difference between said first and second assessment frequencies, wherein said second differential is an absolute value of a difference between said third and fourth assessment frequencies, and wherein satisfaction of said first threshold comprises said second differential being at least a predetermined amount larger than said first differential.

15. The method of claim 14, wherein satisfaction of said first threshold comprises said second differential being at least 15% larger than said first differential.

16. The method of claim 14, wherein satisfaction of said first threshold comprises said second differential being at least 30% larger than said first differential.

17. A method for identifying surface defects on a part, comprising the steps of:

identifying first and second assessment frequencies in a baseline frequency response that encompasses a first surface acoustical wave (SAW) mode;

selecting a reference frequency that is between said first and second assessment frequencies in said baseline frequency response;

exciting a part-under-test using at least one input frequency;

acquiring a frequency response of said part-under-test to said exciting step and that defines a part-under-test frequency response;

identifying third and fourth assessment frequencies in said part-under-test frequency response that encompasses a corresponding first SAW mode, wherein said identifying third and fourth assessment frequencies step comprises deriving values for said third and fourth assessment frequencies such that an area of said part-under-test frequency response between said third and fourth assessment frequencies is equal to an area of said baseline frequency response between said first and second assessment frequencies;

comparing a relationship between the same said reference frequency within said part-under-test frequency response and each of said third and fourth assessment frequencies within said part-under-test frequency response; and characterizing said part-under-test as being defective based upon satisfaction of a surface defect trigger condition, wherein at least part of said surface defect trigger condition is satisfied when said comparing step identifies a predetermined relationship between said reference frequency and each of said third and fourth assessment frequencies.

18. The method of claim 17, wherein said comparing step comprises comparing a first differential between said reference frequency and said third assessment frequency with a second differential between said fourth assessment frequency and said reference frequency.

19. The method of claim 18, wherein said predetermined relationship for said surface defect trigger condition comprises said first differential satisfying a first threshold with respect to said second differential.

20. The method of claim 19, wherein said first threshold requires said first differential to be at least 100% larger than said second differential.

21. The method of claim 19, wherein said first threshold requires said first differential to be at least 150% larger than said second differential.

22. The method of claim 19, wherein said first threshold requires said first differential to be larger than said second differential by at least a predetermined amount.

23. The method of claim 22, wherein said fourth assessment frequency is larger than said third assessment frequency, and wherein said reference frequency is between said third and fourth assessment frequencies.

24. A method for identifying a surface defect on a part, comprising the steps of:

exciting a part-under-test using at least one input frequency;

acquiring a frequency response of said part-under-test to said exciting step and that defines a part-under-test frequency response;

identifying a first surface acoustical wave (SAW) mode in said part-under-test frequency response;

comparing a first SAW mode area in said part-under-test frequency response to a baseline SAW mode area of a baseline frequency response, wherein said comparing step comprises:

identifying first and second assessment frequencies for said baseline SAW mode area within said baseline frequency response;

identifying third and fourth assessment frequencies for said first SAW mode area within said part-under-test frequency response, wherein said identifying step for said third and fourth assessment frequencies for said first SAW mode area comprises deriving values for said third and fourth assessment frequencies such that said first SAW mode area is equal to said baseline SAW mode area; and selecting a reference frequency between said first and second assessment frequencies within said baseline frequency response; and assessing said part-under-test for a defect using said comparing step, wherein said assessing step comprises comparing a relationship between said reference frequency within said part-under-test frequency response and each of said third and fourth assessment frequencies for said first SAW mode area.

25. The method of claim 24, wherein said reference frequency is about midway between said first and second assessment frequencies for said baseline SAW mode area.

26. The method of claim 24, wherein an area of said baseline frequency response between said first assessment frequency and said reference frequency is at least substantially equal to an area of said baseline frequency response between said reference frequency and said second assessment frequency.

27. The method of claim 24, further comprising:

characterizing said part-under-test as being defective based upon satisfaction of a surface defect trigger condition, wherein at least part of said surface defect trigger condition is satisfied when a first differential between said reference frequency and said third assessment frequency for said first SAW mode area satisfies a first threshold that is based upon a second differential between said fourth assessment frequency for said first SAW mode area and said reference frequency.

28. The method of claim 27, wherein said first threshold requires said first differential to be at least 100% of said second differential.

29. The method of claim 27, wherein said first threshold requires said first differential to be at least 150% of said second differential.

30. The method of claim 27, wherein said first threshold requires said first differential to be larger than said second differential by at least a predetermined amount.

31. The method of claim 27, wherein said fourth assessment frequency is larger than said third assessment frequency, and wherein said reference frequency is between said third and fourth assessment frequencies.

* * * * *